(12) United States Patent
Vachtenberg

(10) Patent No.: US 8,628,325 B2
(45) Date of Patent: *Jan. 14, 2014

(54) EXPANDABLE DENTAL IMPLANTS OF HIGH SURFACE AREA AND METHODS OF EXPANDING THE SAME

(75) Inventor: Oz Vachtenberg, Tel-Aviv (IL)

(73) Assignee: Dentack Impants Ltd., Kfar-Saba (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/457,786

(22) Filed: Apr. 27, 2012

(65) Prior Publication Data

US 2013/0108983 A1 May 2, 2013

Related U.S. Application Data

(63) Continuation of application No. 12/439,500, filed as application No. PCT/IB2007/002396 on Aug. 22, 2007, now Pat. No. 8,167,619.

(30) Foreign Application Priority Data

Sep. 3, 2006 (IL) .......................................... 177848

(51) Int. Cl.
  *A61C 8/00* (2006.01)
(52) U.S. Cl.
  USPC ...................................... 433/173; 623/17.17
(58) Field of Classification Search
  USPC ......... 433/172–176, 201.1; 623/17.11, 17.17; 606/68, 300–313, 63, 326; 292/251; 600/184, 186, 220–222; 411/69, 80.5, 411/80.6
  See application file for complete search history.

(56) References Cited

U.S. PATENT DOCUMENTS

| | | | |
|---|---|---|---|
| 4,474,516 A | | 10/1984 | Schiefer |
| 5,004,421 A | | 4/1991 | Lazarof |
| 5,087,199 A | | 2/1992 | Lazarof |
| 5,098,292 A | | 3/1992 | Lazarof |
| 5,417,569 A | | 5/1995 | Perisse |
| 5,611,688 A | | 3/1997 | Hanosh |
| 5,681,167 A | | 10/1997 | Lazarof |
| 5,762,500 A | | 6/1998 | Lazarof |
| 5,782,918 A | | 7/1998 | Klardie et al. |
| 5,931,674 A | * | 8/1999 | Hanosh et al. ................ 433/173 |
| 6,007,337 A | | 12/1999 | Bauer |
| 6,129,763 A | | 10/2000 | Chauvin et al. |
| 6,142,782 A | | 11/2000 | Lazarof |
| 6,213,774 B1 | | 4/2001 | Lazarof |
| 6,332,778 B1 | | 12/2001 | Choung |

(Continued)

OTHER PUBLICATIONS

International Search Report and Written Opinion for International Application No. PCT/IB07/02396; mailing date May 19, 2008; 6 pages.

*Primary Examiner* — Cris L Rodriguez
*Assistant Examiner* — Edward Moran
(74) *Attorney, Agent, or Firm* — Rathe Lindenbaum LLP

(57) ABSTRACT

A dental implant system for placement within a jaw of a patient includes an envelope including an outer surface and an inner surface defining a barrel. At least one barrier is located in the barrel. The barrel having a first region on one side of the barrier and a second region on an opposing side of the barrier. An expander member is movable within the barrel along a longitudinal axis of the barrel from the first region to the second region. The barrier prohibits the expander member from moving from the second region to the first region.

19 Claims, 21 Drawing Sheets

(56) References Cited

U.S. PATENT DOCUMENTS

| | | |
|---|---|---|
| 6,955,691 B2 | 10/2005 | Chae et al. |
| 7,118,598 B2 | 10/2006 | Michelson |
| 2004/0249466 A1 | 12/2004 | Liu et al. |
| 2005/0042573 A1 | 2/2005 | Lustig et al. |
| 2005/0042574 A1 | 2/2005 | Lazarof |
| 2006/0106416 A1 | 5/2006 | Raymond et al. |
| 2006/0194171 A1 | 8/2006 | Lazarof |

\* cited by examiner

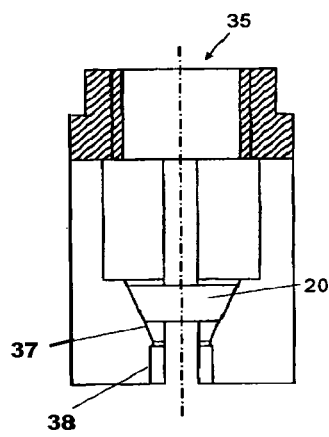 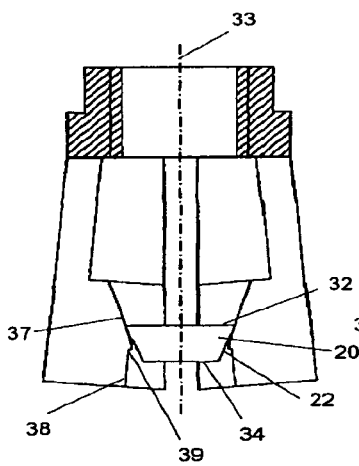 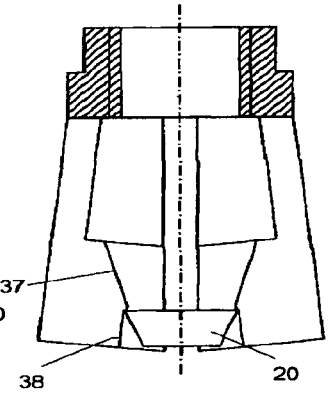
Fig. 6a     Fig. 6b     Fig. 6c
*FIG. 6*

EXPANDABLE DENTAL IMPLANTS OF HIGH SURFACE AREA AND METHODS OF EXPANDING THE SAME

RELATED APPLICATION

This application is a continuation of U.S. patent application Ser. No. 12/439,500 filed Feb. 27, 2009 now U.S. Pat. No. 8,167,619 which is a national state application of Patent Cooperation Treaty Application No. PCT/IB2007/002396 filed Jan. 29, 2007, which claims priority to Israeli Patent Application No. 177848 filed Sep. 3, 2006 each of which is hereby incorporated in its entirety.

FIELD OF THE INVENTION

The present invention pertains to expandable dental implants of high surface area and to methods of in situ expanding the same.

BACKGROUND OF THE INVENTION

Endosseous root form implants-hereinafter referred to as "implants"—are well known devices, which are adapted to support and receive dental prosthetic pieces. Root form implants are generally cylindrical, with a surface area designed to promote good attachment to the jawbone. Most implants are made of titanium or of a titanium alloy, due to the biocompatibility and high rate of osseointegration, i.e. the physiological process of fusing with a living bone, of such a material.

Non-expandable implants have a continuous, cylindrically shaped body, which is threadedly fitted or press-fitted in a bore drilled within a jawbone. The prosthetic piece may not be received in the implant for a period of approximately five months, until bone tissue of the jawbone grows and eventually fuses with the implant, causing discomfiture to a patient and necessitating several visits to an oral surgeon. During this period, bone resorption is noticeable, due to the lack of pressure normally applied by the extracted tooth onto the bone tissue. At times, the bore is improperly drilled, and is much larger than the fixed diameter of the implant. As a result, the implant will not be properly secured to the jawbone. Micro-movement of the implant relative to the wall of the bore is another cause of implant looseness.

The use of an expandable implant, whereby the outer diameter of the implant relative to the wall of the bore is adjustable, obviates the aforementioned disadvantages of non-expandable implants. By providing a controlled amount of lateral expansion, the outer surface of the implant is in pressured, frictional engagement with the jawbone. The degree of frictional engagement with the jawbone is increased by the shape of an expanded implant, which is similar to that of the root of a tooth. Therefore the implant may receive a corresponding prosthetic piece and provide sufficient functional loading for mastication immediately after expansion of the implant, due to the securing of the implant to the jawbone. When a prosthetic piece is attached to the implant immediately following a tooth extraction, bone tissue growth, and consequently osseointegration, is induced by blood flow in the jawbone, the rate of which is substantially equal to the blood flow rate prior to tooth extraction. A substantially unchanging blood flow rate in the jawbone increases the rate of implant osseointegration with the jawbone. Exemplary expandable implants are disclosed in U.S. Pat. Nos. 3,708,883, 5,004,421, 5,470,230, 5,489,210, 5,931,674, 5,951,288 and 6,506,051.

The lateral expansion of the prior art implants is effected by a tubular envelope having deformable elements at the apical end thereof and by an expander member, generally of a frusto-conical shape, in engagement with said deformable elements. As the expander member is displaced along the longitudinal axis of the tubular member, the expander member forces the deformable elements to expand outwardly against the interior sidewall of the jawbone hole.

The securing means, by which the expander member of the prior art expandable implants is secured to the tubular member, is formed longitudinally above the expander. That is to say, the length of an implant is increased due to the arrangement of the securing means relative to the expander member. A short implant is of particular importance for those patients having thin-walled or deformed jawbones, e.g. due to osteoporosis or bone resorption, since a bore drilled in the jawbone in order to receive a normally sized implant of the prior art is liable to injure the mandibular nerve or penetrate the sinus lining. Approximately 20-30% of those patients who require dental implants have thin-walled or deformed jawbones, and therefore these patients are precluded from receiving prior art dental implants.

Prior art dental implants generally have a tubular barrel, which is screwed into a bore formed in a jawbone, having a plurality of radial slits formed at the end which enters furthest into the bore and threads formed on its interior surface. An expander screw has a frusto-conically shaped end surface and a cylindrical outer surface positioned between coronal threads and the end surface. The expander screw is shaped to engage and mate with the threads formed on the interior surface of the barrel, such that advancement of the expander screw along the barrel toward the insertion end causes an end surface of the expander screw to collide with the interior surface of the barrel and to expand the insertion end outward into the surrounding bone. The slits reduce the available barrel surface area that engages the sidewall of the bore, and also weaken the structure of the implant. Due to the reduced structural strength of the implant, each leg of the barrel formed between adjacent radial slits may twist and sever upon removal of the implant, if implant removal is deemed necessary.

Furthermore, the exterior surface of the barrel, which is not immobilized, is liable to be loosened from the sidewall of the jawbone bore over the course of time. Since the expander screw mates with the threading formed on the interior surface of the barrel, reverse rotation of the expander screw, i.e. in a rotational direction opposite to that which causes the barrel to press into the sidewall of the jawbone, due to inter jaw dynamic compressive forces and fluctuating stresses, results in a loosening of the implant.

BRIEF DESCRIPTION OF THE DRAWINGS

In order to understand the invention and to see how it may be implemented in practice, a plurality of preferred embodiments will now be described, by way of non-limiting example only, with reference to the accompanying drawings, in which FIG. 1 schematically presents a perspective view of a dental implant, according to one embodiment of the invention;

FIG. 6a is a longitudinal cross-sectional views of a dental implant, according to another embodiment of the invention, showing a first stage of apical displacement of an expander member.

FIG. 6b is a longitudinal cross-sectional views of a dental implant, according to another embodiment of the invention, showing a second stage of apical displacement of an expander member.

FIG. 6c is a longitudinal cross-sectional views of a dental implant, according to another embodiment of the invention, showing a third stage of apical displacement of an expander member.

SUMMARY OF THE INVENTION

Figure 1:
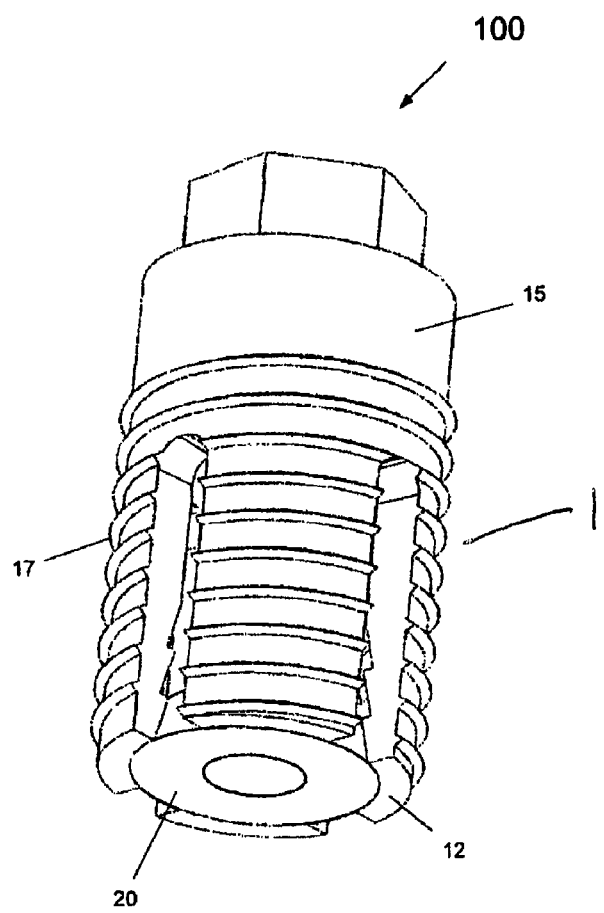

In one embodiment a dental implant system for placement within a jaw of a patient, includes an envelope and a movable expander. The envelope includes an outer surface and an inner surface defining a barrel. At least one barrier is located in the barrel. The barrel includes a first region on one side of the barrier and a second region on an opposing side of the barrier. The expander member is movable within the barrel along a longitudinal axis of the barrel from the first region to the second region. The barrier prohibits the expander member from moving from the second region to the first region.

In another embodiment a dental implant for placement within a jaw of a patient includes an envelope having a barrel extending therethrough. The envelope has a radially expandable portion movable from a contracted configuration to an expanded configuration. The radially expandable portion includes at least one wall element defining an indentation in the expandable portion. The wall element has a folded portion in the contracted configuration and unfolds as the radially expanded portion moves from the contracted configuration to the expanded configuration.

In still another embodiment a dental implant for placement within a jaw of a patient includes an envelope having a barrel extending therethrough. The envelope has a radially expandable portion movable from a contracted configuration to an expanded configuration. The radially expandable portion includes at least one slit having a lid at least partially located therein. The lid extends from a longitudinal edge of the radially expandable portion and covers at least a portion of the slit as the radially expandable portion moves from the contracted configuration to an expanded configuration.

In still another embodiment a method for securing a dental implant in a jaw of a patient includes providing an elongated envelope having a barrel defining a longitudinal axis extending therethrough. The barrel has a first region with a first diameter and a second region with a second diameter less than the first diameter, the barrel includes at least one step with a ledge portion extending away from the longitudinal axis. An expander member is movable within the barrel.

A portion of the envelope is expanded from a contracted position to an expanded position by moving the expander member within the barrel along the longitudinal axis from the first region to the second region. A portion of the expander is secured with the barrier thereby prohibiting the expander from moving from the second region toward the first region.

In a further embodiment, a method 23 for securing a dental implant in a jaw of a patient includes providing an elongated envelope having a barrel defining a longitudinal axis extending therethrough. The barrel has a first region with a first diameter and a second region with a second diameter less than the first diameter. The barrel includes at least one step having a ledge portion that extends away from the longitudinal axis. An expander member is movable within the barrel that expands a portion of the envelope from a contracted position to an expanded position by moving the expander member within the barrel along the longitudinal axis from the first region to the second region. A portion of the expander is secured by the barrier prohibiting the expander from moving from the second region toward the first region.

It is hence one object of the present invention to disclose a self-contained expandable implant (100), comprising: (a) a threadless elongated envelope (1) spanning along a main longitudinal axis (H); transformable from an initial contracted configuration to an expanded configuration; (b) at least one threadless conical expander (20) longitudinally displaceable within the envelope (1) from a coronal position to an apical position or vice versa; such that the expander is thrusted by a pusher along the main longitudinal axis, the expander is tightly fitted into the envelope in a singular predetermined position; wherein the expander is forcefully yet not rotatably immobilized by a lock mechanism integrally incorporated within the envelope; and further wherein the combination of the envelope (1) module and the expander (20) modules is sufficient to secure the implant (100) in the expanded configuration. This implant may be especially adapted for short implants preferably of about 5 to 16 mm. The fact that the immobilizing mechanism is one with the implant's envelope and lies within the radial horizontal plane of the envelope, allows further to develop short implants as detailed above. Thus, this short implant may further especially be adapted to be implanted in thin-walled or deformed jawbones. The expandable implant (100) has a coronal portion attachable to a prosthetic piece.

It is a second object of the present invention to disclose an expandable implant (100) adapted to maximize the surface area between the implant and the jawbone of a patient, comprising: (a) an elongated envelope (1) that spans along a main longitudinal axis; transformable from an initial contracted configuration having $S_0$ (S is the external surface area of the implant) to an expanded configuration $S_1$, (b) threadless inner barrel, its coronal diameter is greater than its apical diameter; (c) at least one step (P) located in said envelope's (1) barrel; said step is characterized by side (L); depth ($T_Y$) wherein 0.01 mm<$T_Y$>1 mm, and angle (θ) wherein 25 degrees<θ>150 degrees, defining slope of side (L) wherein 0.05 mm<L>3 mm; said envelope comprising at least one slit (4), exceeding along said main longitudinal axis from said implant's apical end; and (e) at least one lid (5), at least partially covering the slit (4) in the expanded configuration; and (f) at least one conical expander (20) having coronal diameter ($20D_C$) and apical diameter ($20D_A$), so as $20D_C \geq 20D_A$ or so as $20DA \geq 20D_C$; the expander (20) is vertically displaceable within the envelope (1) from a first coronal position to a second apical position; the step is located between the coronal to the apical locations; within the coronal position, the expander (20) is supported on the at least one step (P), and the apical diameter of the implant (100) is $S_0$; the expander (20) may be thrusted apically by a pusher along the main longitudinal axis, it is forcefully immobilized within the apical location by the step, while increasing the apical diameter of the implant (100) to a predetermined S1; wherein the outer surface area of the implant (100) in the expanded configuration is larger than its outer surface area in the contracted configuration and the implant is tightly fitted into the jawbone.

Within the scope of the present invention is an implant (100) having a rounded cross section, or a polygonal cross-section. The expandable implant therein having a main longitudinal axis H, wherein the length of H is from about 5 mm<H>16 mm. The expandable implant has an initial surface area $S_0$, wherein the difference (ΔS) between the initial surface $S_0$ and the expanded surface S1 is 8%≤Δ S≥30% and especially 8 to 25%. The implant's envelope (1) has an internal diameter wherein 3.2<d>7 mm. The implant's envelope comprises of N slits, N is an integer number equal or higher one, especially 2<N>6. The expandable implant, wherein the cross section of the slit is smooth, is lacerated or concave. The expandable implant, wherein the lid is at least partially integrated within the envelope. In a preferred embodiment of the invention the lid may be also physically connected, glued, welded, punched, screwed, nailed or mechanically connected to the envelope. It may, at least partially, be constructed of metal alloys: especially non-alloy titanium and titanium-based alloys, stainless steel, composite materials, polymers, or any combination thereof. The cross section of the lid may be selected from a group including omega-shaped, w-shaped, v-shaped, accordion-shaped, wave-shaped or any combination thereof. The lateral faces of the lid may be continuous or alternatively at least a portion of the lateral face of the cover is not continuous, e.g., comprising a plurality of apertures. The lid (5a) may be at least partially connected to the side wall of the envelope (1), moving freely in and out of a recess 7, in the facing wall of the envelope. The expandable implant may be comprised at least partially of non alloys, metal alloys, especially non-alloys titanium, titanium-based alloys, stainless steel, composite materials, polymers or any combination thereof.

It is in the scope of the present invention implant to teach that the expander (20) is displaced along the main longitudinal axis of envelope (1) in a vertical manner. It is further in the scope of the present invention implant to teach that the expander (20) expands the apical portion of the envelope (1). During the implant's expansion the slits (4) are at least partially uncovered by the lids (5). The slits (4) may be at least partially uncovered by the lids (5) in a discrete manner. The exposure of covered parts of the slits may expand the envelope's surface area into the expanded surface $S_1$.

A third object of the present invention is to teach an expandable implant (100). Implant 100 comprises (a) an elongated envelope (1) spans along a main longitudinal axis; being transformable from an initial contracted configuration having $D_0$ (D is cross section diameter) to an expanded configuration $D_1$ so as $D_1 > D_0$; the envelope comprises threadless inner barrel, the coronal diameter is greater than the apical diameter of the barrel; at least one step (P) located in the envelope's (1) barrel; the step is characterized by side (L) wherein 0.05 mm<L>3 mm; depth ($T_Y$) wherein 0.01 mm<Ty>1 mm, and angle (θ) wherein 25 degrees<θ>150 degrees, defining slope of side (L); at least one conical expander (20) having coronal diameter ($20D_C$) wherein 1 mm<$D_C$>6 mm and apical diameter ($20D_A$) wherein 1 mm<$D_A$>6 mm, so as $20D_C > 20D_A$ or $20D_A > 20D_C$; the expander (20) is vertically displaceable within the envelope (1) from a first coronal position to a second apical position or vice versa; the step is located between the coronal to the apical locations; wherein within the coronal position, the expander (20) is supported on at least one step (P), and the apical diameter of the implant (100) is $D_0$; and further wherein the expander (20) is thrusted apically by a pusher along the main longitudinal axis, it is forcefully immobilized within the apical location by the step, while increasing the apical diameter of the implant (100) to a predetermined $D_1$.

It is in the scope of the present invention to disclose that the step (P) may protrude radially into the threadless barrel may also and continuously or discontinuously extended therein.

It is in the scope of the present invention to disclose that the inner barrel of the envelope may contain a plurality of N steps, where N is an integer number equal or higher than 1, especially N equals 2.

It is in the scope of the present invention to disclose that the expander may have a cylindrical, a polygonal or preferably a conical cross section It is in the scope of the present invention to disclose that the expander is compressibly displaced along the main longitudinal axis in a vertical manner, a rotating manner, helical manner or any combination thereof. It is also in the scope of the invention to relate that the expander (20) at least partially comprises compositions selected from a group including metal alloys, especially titanium-based alloys and titanium non alloys, stainless steel, other composite materials, or any combination thereof. The expander may be at least partially rigid.

It is a fourth object of the present invention to disclose an expandable implant (100) adapted to have an extended apical base, comprising a threadless inner barrel, its coronal diameter is greater than its apical diameter; at least one step (P) located in the envelope's (1) barrel; the step is characterized by side (L) wherein 0.05 mm<L>3 mm; depth ($T_Y$) wherein 0.01 mm<Ty>1 mm, and angle (θ) wherein 25 degrees<θ>150 degrees, defining slope of side (L); at least one conical expander (20) having coronal diameter ($20D_C$) wherein 1 mm<$D_C$≥6 mm and apical diameter ($20D_A$) wherein 1 mm<$D_A$>6 mm, so as $20D_C \geq 20D_A$ or $20D_A \geq 20D_C$; the expander (20) is vertically displaceable within the envelope (1) from a first coronal position to a second apical position or vice versa; the step is located between the coronal to the apical locations; wherein within the coronal position, the expander (20) is supported on the at least one step (P), and the apical diameter of the implant (100) is $D_0$; and further wherein the expander (20) is lunged apically by a pusher along the main longitudinal axis, it is forcefully immobilized within the apical location by the step, while increasing the apical diameter of the implant (100) to a predetermined $D_1$. It is in the scope of the present invention to disclose that the expander (20) may be irreversibly plugged within most apical position, and a continuous extended apical base is obtained. It is also in the scope of the present invention to disclose that the extended apical base may be flat. It is also in the scope of the present invention to disclose that the expander (20) is adapted to be displaced apically in a discrete manner over two or more steps.

It is a fifth object of the present invention to disclose a method for securing an expandable implant within a jawbone that comprises; obtaining a self-contained expandable implant (100) with (i) threadless elongated envelope (1) spanning along a main longitudinal axis (H), transformable from an initial contracted configuration to an expanded configuration; and, (ii) at least one threadless conical expander (20) displacing longitudinally within the envelope (1) from a first coronal position to a second apical position or vice versa; such that the thrusting of expander apically by a pusher along the main longitudinal axis tightly fits the expander into the envelope in a singular predetermined position; wherein immobilizing the expander is forcefully, yet not rotatably, by a lock mechanism integrally incorporated within the envelope and further wherein the combination of the envelope (1) module and the expander (20) modules is sufficient to secure the implant (100) in the expanded configuration. Adapting the implant especially for short implants preferably of about 5 to 16 mm. Further adapting the implant to be implanted in thin-walled or deformed jawbones. The fact that the immobilizing mechanism is one with the implant's envelope and lies within the radial horizontal plane of the envelope, allows further to develop short implants as detailed above. The expandable implant (100) having a coronal portion attachable to a prosthetic piece.

It is a sixth object of the present invention to disclose a method for expanding the envelope of the implant, comprising; an expandable implant (100), having (a) an elongated envelope (1) spans along a main longitudinal axis; being transformable from an initial contracted configuration having $S_0$ (S is external surface area) to an expanded configuration $S_1$ so as $S1>S0$; the envelope comprising (i) threadless inner barrel, its coronal diameter is greater than its apical diameter; (ii) at least one step (P) located in the envelope's (1) barrel; the step is characterized by side (L); depth $T_Y$ and angle (θ), defining slope of side (L); (iii) at least one slit (4), exceeding along the main longitudinal axis from the envelope's apical end; and, (iv) at least one lid (5), at least partially covering the slit (4) in the expanded configuration; and, (b) at least one conical expander (20) having coronal diameter ($20D_C$) and apical diameter ($20D_A$), so as $20D_C \geq 20D_A$; or so as $20D_A \geq 20D_C$; the expander (20) is vertically displaceable within the envelope (1) from a first coronal position to a second apical position or vice versa; the step is located between the coronal to the apical locations; wherein within the coronal position, the expander (20) is supported on the at least one step (P), and the apical diameter of the implant (100) remains $S_0$; and further wherein the expander (20) is thrusted apically by a pusher along the main longitudinal axis, it is forcefully immobilized within the apical location by the step, while increasing the apical diameter of the implant (100) to a predetermined $S_1$; (a) pushing the expander at least once by a pusher towards the apical end and displacing the same from the coronal position to the apical position over at least one step; and hence, (b) increasing the apical diameter of the implant (100) and to a predetermined $D_1$, and thus immobilizing the expander in its final apical position; wherein the outer surface area of the implant (100) in the expanded configuration is larger than its outer surface area in the contracted configuration. The expander (20) may be compressibly displaced along the main longitudinal axis in a vertical manner. Expander (20) is expanding the apical portion of the envelope (1) wherein the lids (5) may be at least partially uncovering the slits (4) in a discrete or in a non discrete manner. The present method further discloses that the exposure of covered parts of the slits expand the envelope's surface area into $S_1$.

It is a seventh object of the present invention to disclose a method for immobilizing an expander within an implant's envelope, comprising; an expandable implant (100), that has (a) an elongated envelope (1) that spans along a main longitudinal axis; being transformable from an initial contracted configuration having $D_0$ (D is cross section diameter) to an expanded configuration $D_1$ so as $D_1>D_0$; the envelope comprising (i) threadless inner barrel, diameter of the coronal portion is greater than the diameter of the apical portion; (ii) at least one step (P) located in the envelope's (1) barrel; the step is characterized by side (L); depth $T_Y$ and angle (θ), defining slope of side (L); (iii) at least one slit (4), exceeding along the main longitudinal axis from the envelope's apical end; and, (b) at least one conical expander (20) having coronal diameter ($20D_C$) and apical diameter ($20D_A$), so as $20D_C \geq 20D_A$; or as $20D_A \geq 20D_C$; the expander (20) is vertically displaceable within the envelope (1) from a first coronal position to a second apical position or vice versa; the step is located between the coronal to the apical locations; wherein within the coronal position, the expander (20) is supported on the at least one step (P), and the apical diameter of the implant (100) remains $D_0$; and further wherein the expander (20) is thrustedable apically by a pusher along the main longitudinal axis; pushing the expander at least once by a pusher towards the apical end and displacing the same from the coronal position to the apical position or vice versa, over at least one step; and hence, immobilizing the expander in its final apical position while increasing the apical diameter of the implant (100) to a predetermined $D_1$. The method further discloses a step or steps of slightly, reversibly and instantaneously expanding the envelope to a predetermined $D_2$, so as $D_2>D_1$, while irreversibly expanding the same from $D_0$ to $D_1$. The method further discloses a step or steps of displacing the expander along the main longitudinal axis in a vertical manner, a rotating manner, helical manner or any combination thereof.

It is an eighth object of the present invention to disclose a method of providing a dental implant with an extended apical base comprises an expandable implant (100) with (a) an elongated envelope (1) that spans along a main longitudinal axis; transformable from an initial contracted configuration having $D_0$ (D is cross section diameter) to an expanded configuration $D_1$ so as $D_1 > D_0$; the envelope comprising (i) threadless inner barrel its coronal diameter is greater than its apical diameter; (ii) at least one step (P) located in the envelope's (1) barrel; the step is characterized by side (L); depth ($T_Y$) and angle ($\theta$), defining slope of side (L); (iii) at least one slit (4), exceeding along the main longitudinal axis from the envelope's apical end; and, (b) at least one conical expander (20) having coronal diameter (20130 and apical diameter ($20D_A$), so as $20D_C \geq 20D_A$ or so as $20D_A \geq 20D_C$; the expander (20) is vertically displaceable within the envelope (1) from a first coronal position to a second apical position; the step is located between the coronal to the apical locations; the expander (20) is vertically displaceable inside the envelope (1) from a coronal position to an apical position; the step is located between the coronal to the apical locations; within the coronal position, the expander (20) is supported on the at least one step (P), and the apical diameter of the implant (100) is $D_0$.

The method further teaches thrusting the expander (20) towards the apical end by means of a pusher along the main longitudinal axis, thus, forcefully immobilizing the expander (20) within the apical location by the step (P), increasing the apical diameter of the implant (100) to a predetermined D1; and, irreversibly plugging the expander (20) within a most apical position, so as an extended apical base is obtained. The method further discloses that the obtained extended apical base may be flat. The method further discloses step or steps of displacing the expander (20) apically in a discrete manner over two or more steps (P).

It is a ninth object of the present invention to disclose a method for anchoring a dental implant within a bore drilled in the jawbone of a patient; comprising a self-contained expandable implant (100), having: (a) threadless elongated envelope (1) spanning along a main longitudinal axis (H); the elongated envelope (1) is transformable from an initial contracted configuration having $S_0$ (S is the external surface area of the implant) to an expanded configuration $S_1$; the elongated envelope is transformable from an initial contracted configuration having $D_0$ (D is cross section diameter) to an expanded configuration $D_1$ so as $D_1 > D_0$; the envelope also comprising; the envelope comprising: (i) at least one slit (4), exceeding along the main longitudinal axis from the envelope's apical end; (ii) at least one lid (5), at least partially covering the slit (4) in the expanded configuration; (iii) threadless inner barrel, the depth of barrel wall in its apical portions is greater than its coronal portions; and, (iv) at least one step (P) located in the envelope's (1) barrel; the step is characterized by side (L); depth ($T_Y$) and angle (A), defining slope of side (L); (b) at least one threadless conical expander (20) longitudinally displaceable within the envelope (1) from a first coronal position to a second apical position or vice versa; such that the expander is thrusted apically by a pusher along the main longitudinal axis, the expander is tightly fitted into the envelope in a singular predetermined position; the conical expander (20) having coronal diameter ($20D_C$) and apical diameter ($20D_A$), so as $20D_C \geq 20D_A$ or so as $20D_A \geq 20D_C$; the step is located between the coronal to the apical locations; wherein within the coronal position, the expander (20) is supported on the at least one step (P), and the apical diameter of the implant (100) remains $D_0$; and further wherein the expander (20) is forcefully immobilized within the apical location by the step, while increasing the apical diameter of the implant (100) to a predetermined $D_1$ and to a predetermined $S_1$; wherein the expander is forcefully, yet not rotatably, immobilized by a lock mechanism, especially a step, integrally incorporated within the envelope; further wherein the envelope (1) and the expander (20) are solely required to secure the implant (100) in the expanded configuration; further wherein the expandable implant (100) is adapted especially to maximize the surface area between the implant and the jawbone; and further wherein the expandable implant (100) having an extended apical base when the expander (20) irreversibly plugs into the most apical position.

It is another object of the present invention to disclose a method for securing an expandable implant within a jawbone and for immobilizing an expander within an implant's envelope comprising; (a) obtaining an implant with (I) threadless elongated envelope (1) spanning along a main longitudinal axis (H); the elongated envelope (1) is transformable from an initial contracted configuration having $S_0$ (S is the external surface area of the implant) to an expanded configuration $S_1$; the elongated envelope is transformable from an initial contracted configuration having D0 (D is cross section diameter) to an expanded configuration D1 so as $D_1 > D_0$; the envelope also comprising; the envelope comprising: (i) at least one slit (4), exceeding along the main longitudinal axis from the envelope's apical end; (ii) at least one lid (5), at least partially covering the slit (4) in the expanded configuration; (iii) threadless inner barrel, the depth of barrel wall in apical portions is greater than in coronal portions; and, (iv) at least one step (P) located in the envelope's (1) barrel; the step is characterized by side (L); depth ($T_Y$) and angle (A), defining slope of side (L); and, (II) at least one threadless conical expander (20) longitudinally displaceable within the envelope (1) from a first coronal position to a second apical position or vice versa; such that the expander is thrusted apically by a pusher along the main longitudinal axis, the expander is tightly fitted into the envelope in a singular predetermined position; the conical expander (20) having coronal diameter ($20D_C$) and apical diameter ($20D_A$), so as $20D_C \geq 20D_A$ or so as $20D_A \geq 20D_C$; the step is located between the coronal and the apical locations; wherein in the coronal position, the expander (20) is supported on the at least one step (P), and the apical diameter of the implant (100) remains $D_0$; (a) pushing the expander at least once by a pusher towards the apical end and displacing longitudinally the same within the envelope (1) from the first coronal position to the second apical position over at least one step; tightly fitting the expander into the envelope in a singular predetermined position; (b) increasing the apical diameter of the implant (100) and to a predetermined $D_1$, and thus immobilizing the expander in its final apical position; wherein the outer surface area of the implant (100) in the expanded configuration is larger than its outer surface area in the contracted configuration; and, (c) forcefully immobilizing the expander in its final apical position by the step (P) while increasing the apical diameter of the implant (100) to a predetermined $D_1$, wherein immobilizing the expander is achieved forcefully, yet not rotatably, by a lock mechanism integrally incorporated within the envelope. The method further discloses providing a dental implant with an extended apical base also comprising irreversibly plugging the expander (20) into the most apical position, so as an extended apical base is obtained.

DETAILED DESCRIPTION OF THE PREFERRED EMBODIMENTS

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide expandable dental implants of high surface area and to methods of expanding and anchoring the same in situ.

The term "longitudinal" refers hereinafter to the direction of the long axis or "top-to-bottom" axis.

The term "apical" refers hereinafter to the direction of the dental root or oral cavity.

The term "coronal" refers hereinafter to the direction of the crown of the tooth.

The term "expandable" refers hereinafter to the capability of the implant to increase its lateral dimension.

The term "expander" refers hereinafter to an element that causes expansion, particularly by pressing on the inner surface of an outer body.

The term "immobilized expander" refers hereinafter is an expander that can no longer be longitudinally or laterally displaced.

The term "slit" refers hereinafter to an aperture in the envelope of the implant that can be opened or closed.

The term "lid" refers hereinafter to a part of the envelope covering said slit.

The term "outwards" refers hereinafter to the movement in the direction of the wall of the bore in the jawbone.

The term "inwards" refers hereinafter to the movement in the direction of the longitudinal axis of the implant.

The term "$S_0$" refers hereinafter to the total surface area of the envelope in its initial contracted condition when the slits are covered by the lids.

The term "$S_1$" refers hereinafter to the total surface area of the envelope in its secondary fully expanded condition when the slits are maximally uncovered by the lids.

The term "$D_0$" refers hereinafter to the external diameter of the envelope in its initial contracted condition; wherein d is the internal diameter of the same.

The term "$D_1$" refers hereinafter to the diameter of the envelope in its secondary fully expanded condition.

The term "contracted configuration" refers hereinafter to the initial closed/shrunk configuration of the implant.

The term "expanded configuration" refers hereinafter to the secondary enlarged, opened configuration of the implant.

The term "lock mechanism" refers hereinafter to the state of the expander inside the envelope where it is positioned and trapped by a step.

The term "pusher" refers hereinafter to the external mean provided to force the expander to displace inside the inner barrel of the envelope.

The term "step" refers hereafter to a recess or protruding barrier which a lock mechanism may latch onto.

The term "about" refers hereafter to ±20% of the defined measure.

The present invention, according to one of its embodiments, depicts an expandable dental implant used to achieve maximal contact area and optimal anchoring of the implant inside the jawbone.

The implant is assembled of essentially two components; an elongated envelope that spans along a main longitudinal axis; transformable from an initial contracted configuration having a limited minimal external surface area to an expanded configuration where the envelope's total surface area is greater. The implant's envelope has at least one slit, exceeding along the implant's main longitudinal axis starting from the apical end; and at least one lid which at least partially covers the slit in the expanded configuration. The surface area of the expanded dental implant is larger than the surface area in the initial contracted configuration. In a preferred embodiment of the invention the expandable dental implant has a rounded cross section. The expandable dental implant has a polygonal cross section according to another preferred embodiment of the invention. The expandable implant has a main longitudinal axis H, with a length of about 5 to 16 mm, an initial inner barrel diameter, d, of about 3.2 to 7 mm according to one embodiment of the invention. The expandable implant in its expanded condition has an enlarged surface area $S_1$ wherein the difference ($\Delta S$) between the initial $S_0$ and the expanded $S_1$ is $8\% \leq \Delta S \geq 30\%$ according to another embodiment of the invention.

The expandable implant has in its envelope N number of N slits, where N is an integer number equal or higher to one, preferably but not necessarily 2<N>6. When depicting a horizontal cross section of the slit it can be formed as smooth, lacerated or concave. The slits in the expandable implant's envelope are exposed according to one embodiment of the invention. The slit in the expandable implant's envelope are at least partially covered by a lid which is at least partially integrated within said envelope, in the form of folds or pleats, according to another embodiment of the invention. The lid covering the slits is physically connected, glued, welded, punched, screwed, nailed, or mechanically interconnected to the implant's envelope according to another embodiment of the invention.

The lid partially covering the slit in the implant's envelope has a cross section selected from a group including omega-shaped, w-shaped, v-shaped, accordion-shaped, wave-shaped or any combination thereof.

The lid partially covering the slit in the implant's envelope has a continuous lateral face according to one embodiment of the invention. The lid partially covering the slits in the implant's envelope has at least a portion of the lateral face is not continuous, e.g., comprising a plurality of apertures according to another embodiment of the invention.

The lid partially covering the slit in the implant's envelope is immobilized partially to one side of the slit, moving freely in and out of a recess 7, in the envelope's wall, according to another embodiment of the invention.

The expandable implant can be manufactured at least partially from metal alloys, especially titanium-based alloys; titanium based non alloys, stainless steel, composite materials, polymers or any combination thereof.

The lid covering the slits is manufactured at least partially from metal alloys, especially titanium-based alloys, titanium non alloys, stainless steel, composite materials, polymers, or any combination thereof according to one embodiment of the invention. The lid covering the slits is manufactured at least partially from flexible materials, especially polymers, composite materials, or any combination thereof according to another embodiment of the invention.

The expandable implant depicted in the invention is expanded by two components: the envelope 1, being transformable from an initial contracted configuration having across section diameter of $D_0$, to an expanded configuration where the diameter is $D_1$, so as $D_1 \geq D_0$.

The envelope 100, has a threadless inner barrel, the thickness of the envelope's wall in its apical portion is greater than in its coronal portion. Located inside the envelope's inner barrel there is at least one step P. Step P is characterized by side L, depth $T_y$, wherein Ty is between about 0.01 to 1 mm, and angle ($\theta$) is between about 25 degrees to 150 degrees, defining slope of side (L) ranging from about 0.05 mm to 3 mm. The expandable implant has at least one conical expander 20, located inside the inner barrel, having coronal diameter $20D_C$, where 1 mm<$20D_C$>6 mm, and apical diameter $20D_A$, where 1 mm<$20D_A$>6 mm, so as $20D_C \geq 20DA$ according to one embodiment of the invention, or $20D_C \geq 20D_A$ according to yet another embodiment of the invention.

According to another embodiment of the present invention, the expander 20 is vertically displaceable within the envelope 1, from a first coronal position to a second apical position, or vice versa, by a pusher. The step P is located between the coronal and the apical positions. When the expander 20, is in the initial coronal position it is supported on at least one step P, and the apical diameter of the implant 100 is $D_0$. When the expander 20 is thrusted apically by the pusher along the main longitudinal axis, it is forcefully immobilized in the apical location by the step. As the diameter of the expander is larger than the diameter of the inner barrel in the apical position, this displacement expands the implant by increasing its apical diameter to the predetermined expanded diameter $D_1$.

According to another embodiment of the present invention, the step P located inside the threadless inner barrel of the envelope protrudes radially from its wall according to one embodiment of the invention. According to another embodiment of the present invention, the step P located inside the threadless inner barrel of the envelope protrudes radially from its wall and continuously extended therein according to another embodiment of the invention. The step P located inside the threadless inner barrel of the envelope protrudes radially from its wall and discontinuously extended therein according to another embodiment of the invention.

The inner barrel of the implant's envelope has a plurality of N steps, N is an integer number equals to or higher than 2 according to one embodiment of the invention. The inner barrel of the implant's envelope has a plurality of N steps, where N equals 2 or according to another embodiment of the invention. The inner barrel of the implant's envelope has a plurality of N steps, where N equal 3 according to another embodiment of the invention.

The expander located inside the barrel of the implant's envelope having a cylindrical cross section according to one embodiment of the invention. The expander located inside the barrel of the implant's envelope having a polygonal cross section according to another embodiment of the invention. The expander located inside the barrel of the implant's envelope having a conical cross section according to another embodiment of the invention.

According to another embodiment of the present invention, the expander 20 is pushed to its secondary apical position and is permanently immobilized by the steps inside the envelope's inner barrel. In this process, while irreversibly expanding from $D_0$ to $D_1$, the implant's envelope is adapted to slightly, reversibly and instantaneously expand radially to a predetermined diameter $D_2$, so as $D_2$>$D_1$. This slight expanding to the $D_2$ diameter is reversed immediately to the $D_1$ diameter when the expander is located in its apical position under the step. Thus the envelope further immobilizes the expander in this apical position.

According to another embodiment of the present invention, the expander located inside the barrel of the implant is compressibly displaced along the main longitudinal axis in a vertical manner, a rotating manner, helical manner or any combination thereof.

According to another embodiment of the present invention, the expander located inside the barrel of the implant's envelope at least partially manufactured from compositions selected from a group including metal alloys, especially titanium-based alloys, stainless steel, other composite materials, or any combination thereof.

According to another embodiment of the present invention, the expander located inside the barrel of the implant's envelope is at least partially rigid.

The expandable implant in its final expanded position has an extended continuous apical base further increasing the surface area to promote the process of osseointegration and also to eliminate entry of infection into the implant's inner barrel.

The expander 20 located inside the inner barrel of the implant's envelope 1 being in its initial coronal position is supported on at least one step P, and the apical diameter of said implant 100 is $D_0$. When the expander is thrusted towards the apical end by a pusher it is forcefully immobilized within the apical location by the step, while increasing the apical diameter of said implant (100) to a predetermined $D_1$. In this state the expander 20 irreversibly plugs within most apical position, an extended apical base is obtained.

According to another embodiment of the present invention, the expander positioned in the apical end of the implant creates an extended apical flat base.

According to another embodiment of the present invention, the expander positioned in the apical end of the implant is adapted to be displaced apically in a discrete manner over two or more steps.

According to another embodiment of the present invention, the expander 20 located in the initial coronal position is supported on at least one step P, and the apical diameter of said implant 100 is $S_0$. When the expander 20 is thrusted apically by a pusher along the main longitudinal axis, it is forcefully immobilized within said apical location by said step, while increasing the apical diameter of the implant 100 to a predetermined $S_1$. In this expanded configuration the outer surface area of the implant 100 is larger than its outer surface area in the initial contracted configuration. According to another embodiment of the present invention, the process of the enlargement of the envelope's surface area is carried out by of the slits 4 located along the main axis in the apical portion of the implant's envelope 1. As the expander compressibly displaces along said main longitudinal axis to the apical position, the lids 5 are forced to open and uncover the slits, thus unfolding and enlarging the implant's surface area.

According to another embodiment of the present invention a method for immobilizing an expander within an implant's envelope is provided. The method outlines obtaining an expandable implant 100, comprising (a) an elongated envelope 1 that spans from a coronal end to an apical end along a main longitudinal axis; being transformable from an initial contracted configuration having a cross section diameter $D_0$ to an expanded configuration $D_1$ so as $D_1$>$D_0$. The implant's envelope comprises (i) a threadless inner barrel; the thickness of barrel wall in apical portion is greater than the thickness in coronal portions (ii) at least one step P located in the envelope's inner barrel. The step is characterized by side L, thickness $T_y$ and angle $\theta$, defining slope of side L (iii) at least one slit 4, exceeding along said main longitudinal axis from said envelope's apical end; and, (b) at least one conical expander 20 having coronal diameter $20D_C$ and apical diameter $20D_A$, so as $20D_C \geq 20D_A$ or $20D_A \geq 20D_C$. The expander 20 is vertically displaceable within said envelope 1 from a first coronal position to a second apical position, or vice versa, when the step P is located between the coronal and the apical locations. Within the initial coronal position, the expander 20 is supported on at least one step P, and the apical diameter of the implant 100 remains $D_0$. The process of expanding the implant and immobilizing the expander inside the envelope proceeds in a stepwise manner. The expander 20 is thrusted apically at least once by a pusher along the main longitudinal axis over at least one step and hence immobilizing the expander under the step, in its final apical position while increasing the apical diameter of the implant to a predetermined $D_1$.

According to another embodiment of the invention, the method additionally comprises a step or steps of slightly, reversibly and instantaneously expanding the envelope to a predetermined diameter $D_2$, so as $D_2 > D_1$, while irreversibly expanding the same from $D_0$ to $D_1$. The diameter $D_2$ is formed only when the expander moves exactly across the planar axis of the step. Once moving across the step, the over expanded diameter $D_2$ decreases to the predetermined expanded diameter $D_1$. The process of momentarily reversible over-expanding and withdrawing back to $D_1$, further immobilizes the expander within the envelope in the apical position.

According to another embodiment of the invention, the method additionally comprises a step or steps of displacing said expander along said main longitudinal axis in a vertical manner, a rotating manner, helical manner or any combination thereof.

According to another embodiment of the invention, the method additionally comprises obtaining an expandable dental implant having an extended apical base in its final expanded position, thus further increasing the surface area to promote the process of osseointegration and also to eliminate entry of infection into the implant's inner barrel. The expander 20 is vertically displaced within the implant's envelope 1, by thrusting said expander 20 towards the apical end by means of a pusher along the main longitudinal axis, from a first coronal position to a second apical position. The expander is forcefully immobilized under the step P, thus increasing the apical diameter of the implant to a predetermined $D_1$; and, irreversibly plugging the expander 20 within a most apical position, so as an extended apical base is obtained.

According to another embodiment of the invention the expander 20 is displaced over the steps in a discrete manner over two or more steps.

The extended apical base is flat according to another embodiment of the invention.

Reference is now made to FIG. 1 illustrating one preferred embodiment of an expandable dental implant, generally designated as 100. Implant 100 comprises outer envelope 1 and annular either conical expander member 20, which is received in a threadless barrel of envelope 1, when the small diameter side of the expander is directed either towards the apex or towards the corona, and is in contact with envelope's wall 12 thereof. The most coronal portion of the implant 15 is possibly yet not exclusively provided with external threading 17, which facilitates implanting within a bore drilled within a jawbone, or within a recess formed by the extraction of a tooth.

Both envelope 1 and expander 20 are possibly made from a high-strength and biocompatible material, such as titanium or a titanium alloy. Preferably both the body and expander member are made from the same material, so as to prevent corrosion, which normally results from the generation of an electrochemical cell by the placement of two different metals in an aqueous environment, such as blood and saliva, due to the potential difference between the two metals.

The basic format of a dental implant comprising only two components (namely envelope and expander) has a significant advantage over expanding implants of the prior art. The elimination of additional screwing means to move the expander inside the envelope allows for the development of significantly shorter (about 6 to 10 mm) implants that can be used in special cases of thin-walled or deformed jawbones patients.

Figure 2:
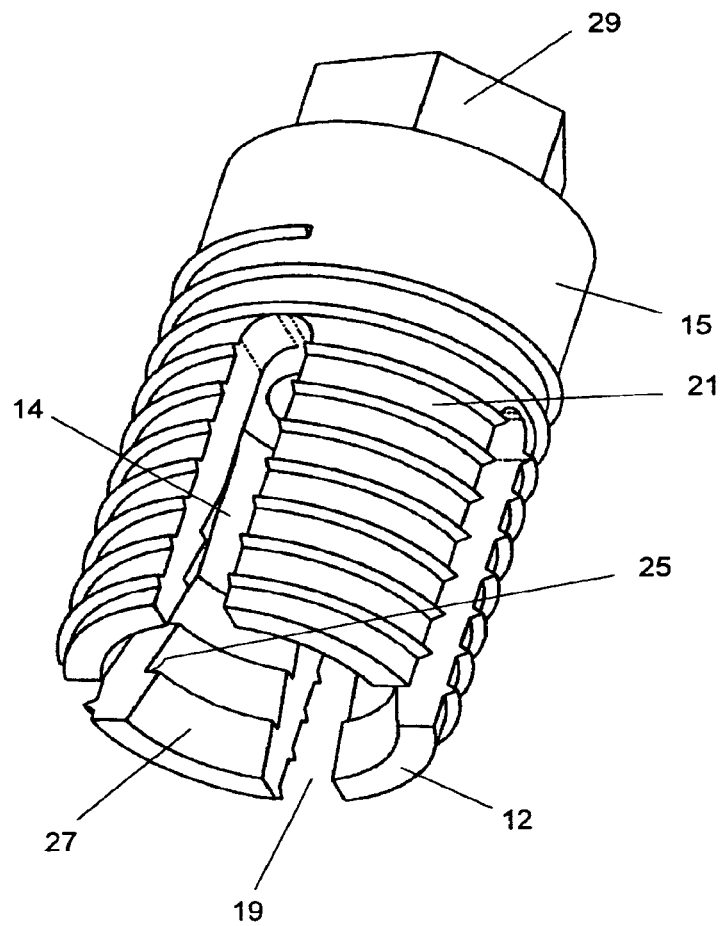
FIG. 2 is a perspective view of the dental implant of FIG. 1, with the expander member removed.

A possible structure of envelope 1 is shown in a non-limiting manner in FIG. 2, without showing expander 20 being accommodated thereto.

A plurality of N narrow longitudinal slits 19 are formed in wall 12 of envelope 1, wherein N is an integer number equal or higher than one. Here e.g., four vertical slits are shown, defining thereby four elastically deformable clasps 21 that are adapted to expand laterally outwards as an expander 20 is longitudinally displaced along the main longitudinal axis of eth implant towards the apical end.

The inner surface 14 of each clasp, at the apical end thereof, is formed with N circumferential steps 25 (also denoted P), e.g., 3 steps. It is in the scope of the invention wherein the steps of each adjacent clasp are coplanar, e.g. the most coronal step of each clasp is coplanar and defines an arc of a circle which is perpendicular to, and whose center coincides with, the longitudinal axis of envelope 1.

The coronal end of envelope 1 is possibly provided with head 29, having e.g., a hexagonal shape as illustrated, or formed with any other convenient shape, preferably yet not exclusively with a smaller width than the outer diameter of wall 12, and serves as an anti-rotation device for a prosthetic piece that is to be secured thereto by e.g., a similarly shaped recessed socket formed in said prosthetic piece.

Inner surface 14 of each clasp 21 is also formed with a plurality of N inclined backs 27, wherein each back is associated with a corresponding step 25. The curvature of four corresponding backs 27 is preferably yet not exclusively substantially equal, selected to be approximately equal to the curvature of the expander member. The inclination of each back is substantially equal to that of the conical 1 expander, placed in either direction, so as to allow for the expander to securely rest against each set of N backs during lateral expansion.

Prior to the implantation of implant 10, expander 20 is press-fitted into the apical end of unexpanded envelope 1, which has an inner diameter substantially equal to that of the outer diameter of the apical end of the expander, and therefore envelope 1 assumes according to one embodiment a tubular shape, as illustrated in an out of scale scheme of FIG. 1.

Figure 3A:
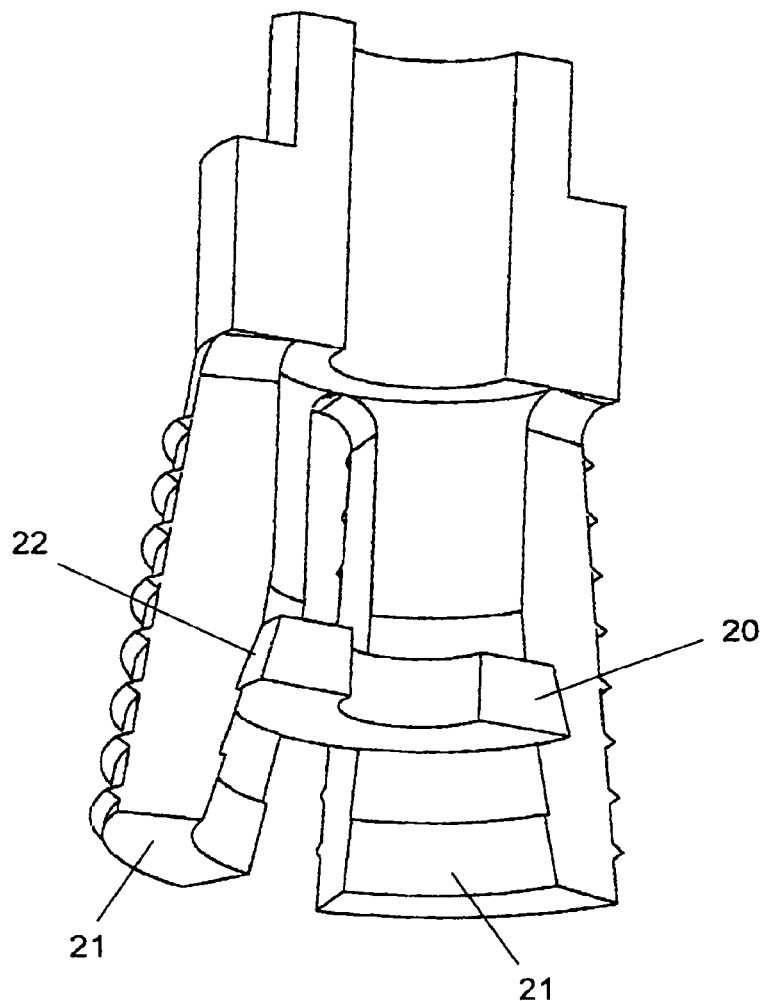
FIG. 3A is a perspective view of an expanded dental implant of FIG. 1, with the outer body partially removed.
Figure 3B:
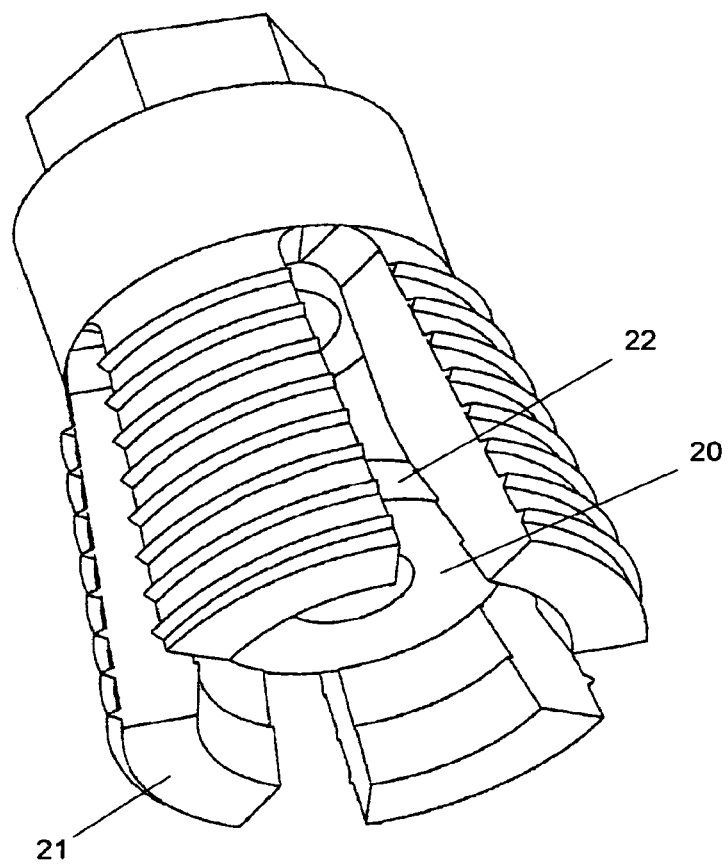
FIG. 3B is a perspective view of an expanded dental implant of FIG. 1.

During coronal displacement of expander 20, as shown in FIGS. 3a and 3b, side 22 of the expander bears against the back of a more coronal step, if existing. Since the outer diameter of the expander is greater than the spacing between diametrically opposite backs of the more coronal step, the apical backs are forced to move outwards, due to the flexibility of clasps 21.

Figure 4:
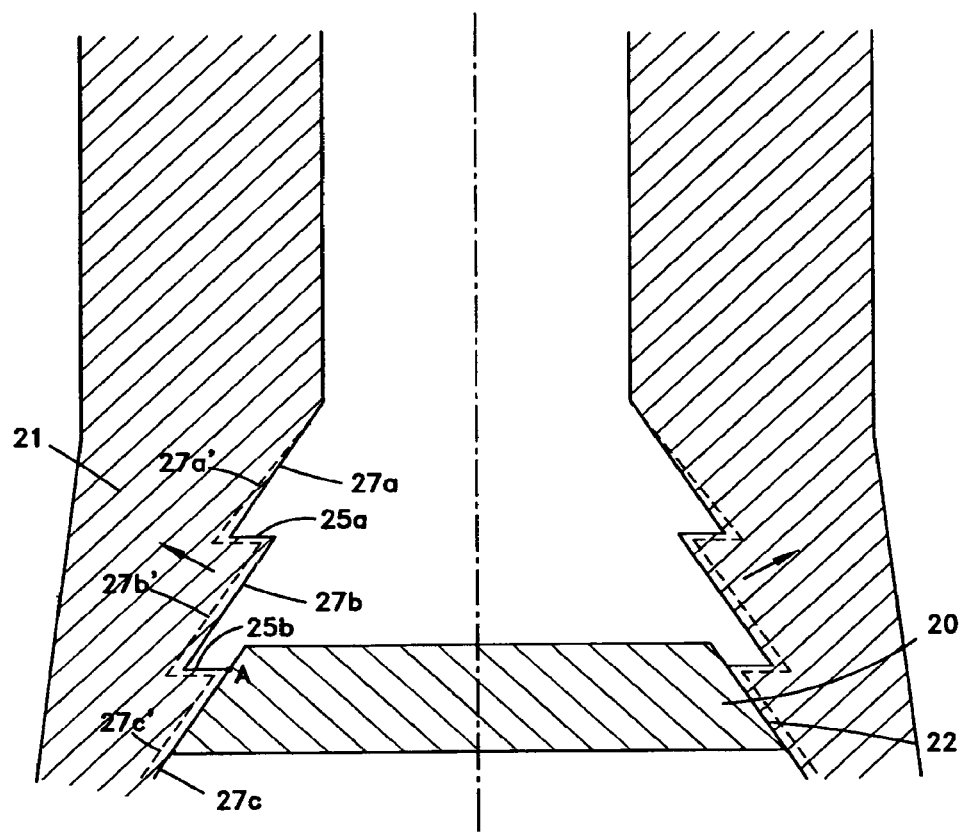
FIG. 4 is a longitudinal cross-sectional view of the implant of FIG. 1, illustrating the expansion of an outer body.

FIG. 4 illustrates the outward expansion of clasps 21 during coronal displacement of expander member 20. Each clasp 21 is formed with a coronal step 25a and coronal back 27a, intermediate step 25b and intermediate back 27b, and apical back 27c, with the inner diameter generated by a coronal step 25a being smaller than that generated by intermediate step 25b. As expander member 20 is coronally displaced, clasps 21 are gradually urged apically outwards. For example, the outer diameter of side 22 at contact point A is greater than the spacing between diametrically opposite apical backs 27c, and consequently the three apical backs are urged apically outwards until being flexed to positions 27a', 27b' and 27c', respectively. Greater coronal displacement of the expander member results in greater outward flexing of the clasps 21.

Figure 5:
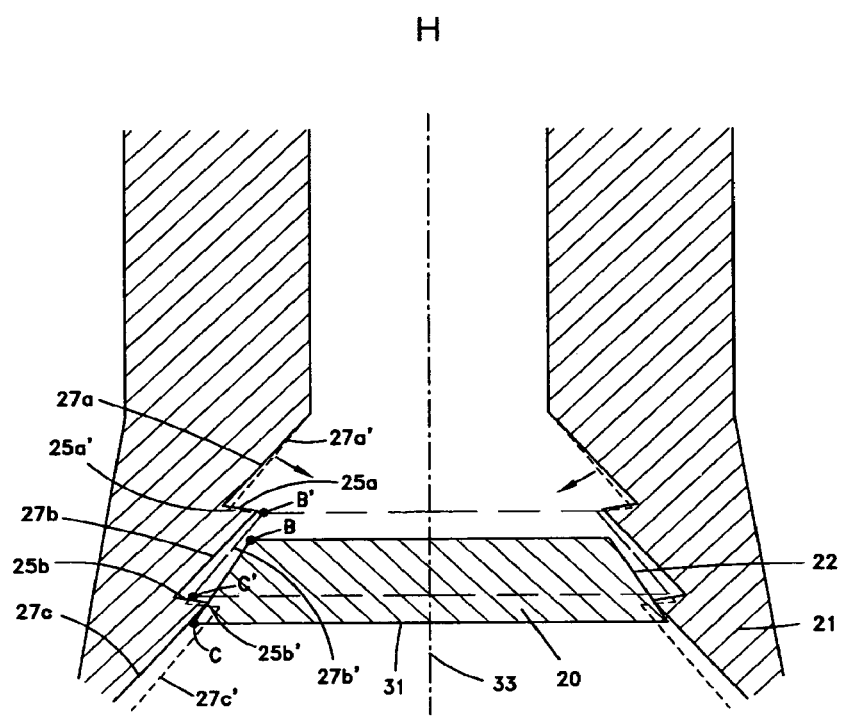
FIG. 5 is a longitudinal cross-sectional view of the implant of FIG. 1, illustrating the immobilization of an expander member.

As expander member 20 is further coronally displaced, as shown in FIG. 5, clasps 21 continue to outwardly expand, due a changing contact point between side 22 and the apical backs 27c. When apical end 31 of the expander member is displaced to point C approximately coincident with, but slightly apical from, intermediate step 25b, backs 27a-c assume the inclination shown by the solid lines relative to longitudinal axis H of the implant. Following additional coronal displacement, apical end 31 of the expander is displaced beyond the coronal end of backs 27c to point C', and backs 27a-c cease to contact the expander. Potential energy stored in the angularly deformed legs 21, which is imparted thereto by the displacing means, as will be described hereinafter, is therefore released when expander member 20 is separated from the inner surface of the legs. Backs 27a-c accordingly tend to return to their original position, as shown in FIG. 4, but are retarded by the expander 20. Backs 27a-c are consequently inwardly displaced, as indicated by the dashed line, following the release of potential energy from each leg 21, until back 27b abuts side 22 of the expander at contact point B' and step 25b abuts the expander member at contact point C'. The backs then assume an inclination relative to axis H, as represented by the dashed lines at 27a'-c'.

Substantially radial forces applied to expander 20 by each leg at corresponding contact points B' and C' prevent the expander member from being apically displaced. When the displacing means is detached from the expander, the latter is also prevented from being longitudinally displaced. As a result, the expander is immobilized, and will not be loosened over the course of time. Conversely, a threaded expander of prior art expandable implants is frictionally restrained by an outer body, and may be rotated in reverse and loosened due to inter jaw dynamic compressive forces or any movement causing vibrations like walking, running or jumping (and fluctuating stresses). Threaded immobilization of prior art implants is dependent solely on frictional forces and coefficients that depend on the materials, surface area texture and the implant's geometry.

It will be appreciated that expander 20 may not be apically displayed from back 27b' to back 27c' by a longitudinal force after being immobilized, since step 25b' supports apical end 31 of the expander, radially extending inwards from side 22. However, the expander may be coronally displaced from back 27b' to back 27a' by the displacing means since step 25a' is oblique to side 22, and therefore back 27b' will be urged outwards by side 22 during coronal displacement of the expander member.

As shown in FIGS. 6a-c, the outer body is also expandable upon apical displacement of the expander. Implant 100, as shown in FIG. 6a before apical displacement of the expander, comprises envelope 1 and frusto-conical expander 20, which is positioned such that its coronal end 32 has a larger diameter than its apical end 34. The inner surface of body 36 at its apical deformable end is formed with a deformable portion 37, which is inclined with respect to axis H of body 36, and a normally straight portion 38 before expansion of the outer body, which is formed apically to inclined portion 37. As expander 20 is apically displaced, as shown in FIG. 6b, outer wall 22 of the expander applies a radial force to the inclined deformable portion 37. Since the apical dimension of the spacing between opposed inclined portions 37 is less than the outer diameter of coronal end 32 of expander 20, portions 37 are flexed in response to the apical displacement of the expander, and body 36 expands. Following additional apical displacement of expander 20, as shown in FIG. 6c, coronal end 32 of the expander member is immobilized by step 39, which is formed apically to inclined portion 37, and by straight portion 38.

FIGS. 7a-c illustrate another preferred embodiment of the present invention, wherein the rigid expander 20 is cylindrical. Implant 100, as shown in FIG. 7a before coronal displacement of the expander, comprises outer tubular body 45 formed with a cylindrical recess 47, which is suitably sized so as to immobilize cylindrical expander 50. The inner surface of body 45 apical to recess 47 is formed with a deformable portion 48, which is inclined with respect to outer wall 51 of the expander. As expander 50 is coronally displaced, as shown in FIG. 7b, outer wall 51 of the expander applies a radial force to the inclined deformable portion 48. Since the apical dimension of the spacing between opposed inclined portions 48 is less than that of expander 50, portions 48 are flexed in response to the coronal displacement of the expander member, and outer wall 42 of body 45 accordingly assumes a concave, parabolic shape, due to the apical expansion thereof. Following additional coronal displacement of expander 50, as shown in FIG. 7c, apical end 53 of the expander is displaced into recess 47. Since deformable portion 48 does not encounter resistance by expander 50, portion 48 is inwardly displaced and wall 46 of recess 47 contacts outer wall 51 of the expander, thereby immobilizing the expander.

FIGS. 8-15 illustrate another preferred embodiment of the invention wherein the outer body is continuous, not being formed with slits and legs. With such a configuration, penetration of infection into the jawbone is prevented. Additionally, in the expanded position, a far larger (by 10-15%) surface area is provided, compared to expandable implants of prior art. Therefore, the process of osseointegration is further promoted. The outer body is deformable, and therefore expandable, due to a novel construction wherein a plurality of thin-walled, curved indentations are formed in the wall of the outer body.

Figure 8:
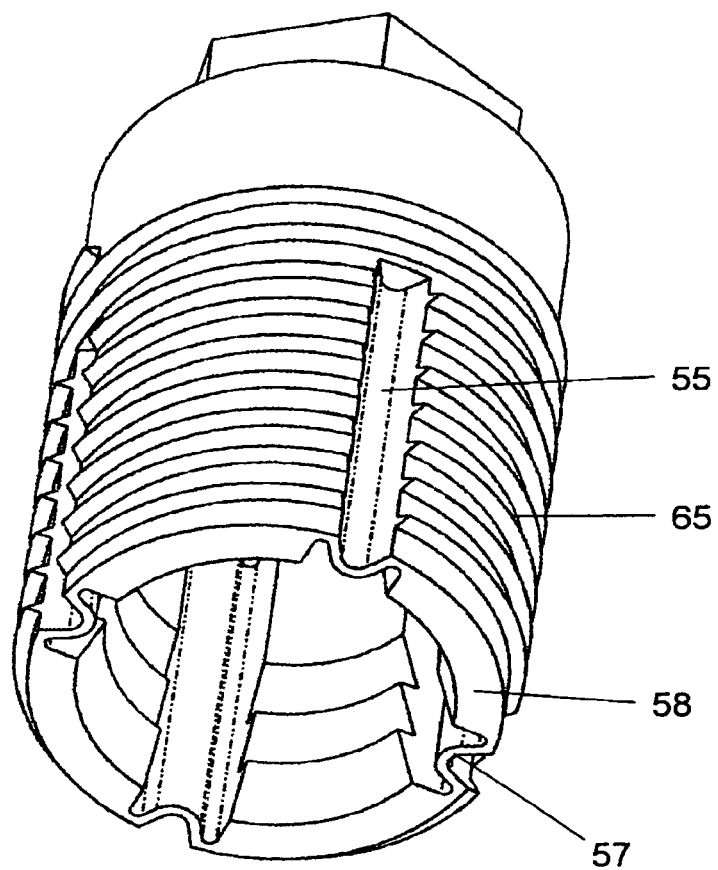
FIG. 8 is a perspective view of a dental implant, according to another embodiment of the invention, shown with the expander member removed.
Figure 9:
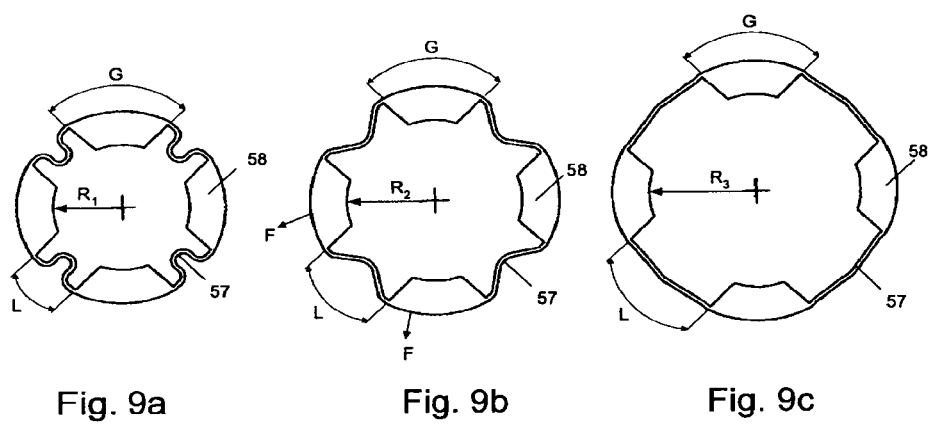
FIG. 9a is a bottom views of the dental implant of FIG. 8, during a first stage of expansion.
FIG. 9b is a bottom views of the dental implant of FIG. 8, during a second stage of expansion.
FIG. 9c is a bottom views of the dental implant of FIG. 8, during a third stage of expansion.

As shown in FIG. 8, tubular outer body 65 is formed with a plurality of equally spaced, longitudinally extending indentations 55. Each indentation 55 is formed by a thin-walled element 57, which is significantly thinner than the relatively thick wall 58 of the remaining portions of outer body 65. When outer body 65 is not expanded, indentations 55 are in a collapsed configuration, with each thin-walled element being curved and facing inwards.

FIGS. 9a-c illustrate the change in shape of an outer body formed with a plurality of indentations, during expansion thereof. When an outer body is unexpanded, as indicated by radius $R_1$ in FIG. 9a, the circumferential length G of a thick-walled portion 58, e.g. one that is formed with steps and backs as described hereinabove, is significantly greater than the circumferential length L of a thin-walled element 57. Upon longitudinal displacement of the expander member, the side of the expander member outwardly presses on each rigid thick-walled portion 58, due to the greater outer diameter of the expander member relative to that of the thick-walled portions. Consequently, thick-walled portions 58 are outwardly displaced to radius $R_2$ as shown in FIG. 9b. Each thin-walled element 57 is outwardly flexed due to the outward force F applied to each thick-walled portion 58 by the expander member. Since a thick-walled portion 58 is connected to an adjacent thin-walled element 57, the outward displacement of a thick-walled portion applies a force to the adjacent thin-walled element, causing the curve of each thin-walled element to be flattened. Upon maximum longitudinal displacement of the expander, the thick-walled portions expand to a radius of $R_3$ as indicated in FIG. 9c, and the thin-walled elements 57 assume the general shape of thick-walled portions 58, with the circumferential length G of a thick-walled portion being substantially equal to the circumferential length L of a thin-walled element.

Figures 10, 10A, 10B, 10C:
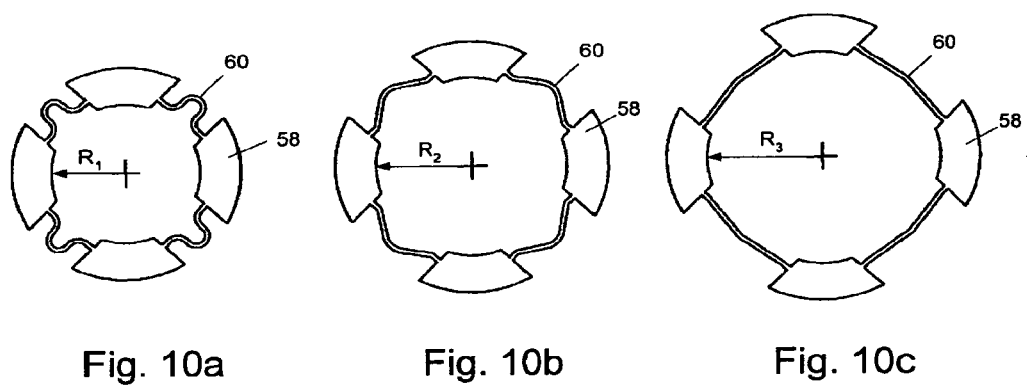
FIG. 10a is a bottom views of a dental implant having indentations formed in the inner surface of the outer body, during a first stage of expansion.
FIG. 10b is a bottom views of a dental implant having indentations formed in the inner surface of the outer body, during a second stage of expansion.
FIG. 10c is a bottom views of a dental implant having indentations formed in the inner surface of the outer body, during a third stage of expansion.

In FIGS. 10a-c, the inner surface of the outer body is formed with a plurality of curved indentations, with the concave side of thin-walled elements 60 facing inwards. Once again, the thick-walled portions 58 are shown to be progressively outwardly expanded, from a minimum radius of $R_1$ to a maximum radius of $R_3$, until thin-walled elements 61 assume the general shape of the thick-walled portions.

Figure 11:
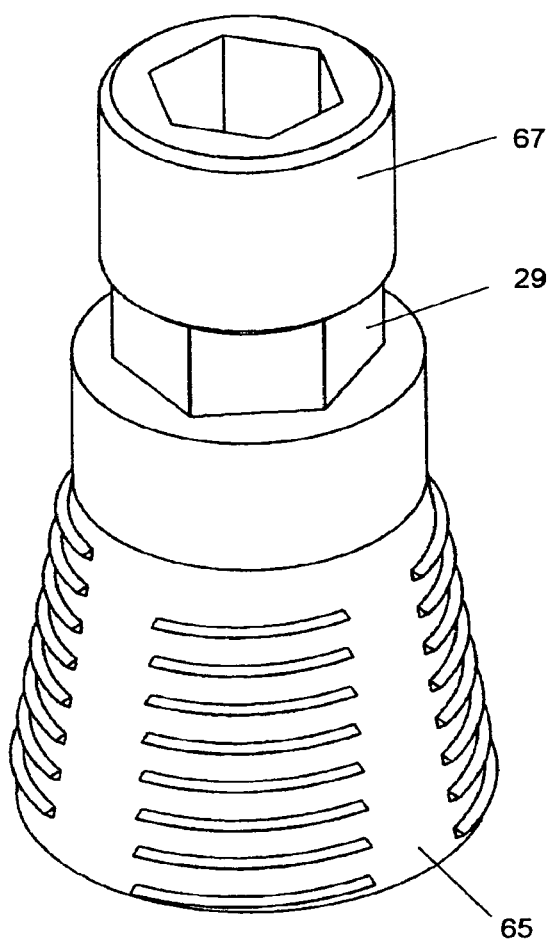
FIG. 11 is a perspective view of an expanded dental implant of FIG. 8.

As shown in FIG. 11, body 65 is frusto-conical when expanded. The longitudinal displacement means may be a screw engaged by threading the formed internally to the expander member. Head 67 of the screw is also shown, and is supported during rotation by hexagonal head 29 attachable to a prosthetic piece.

Figure 12:
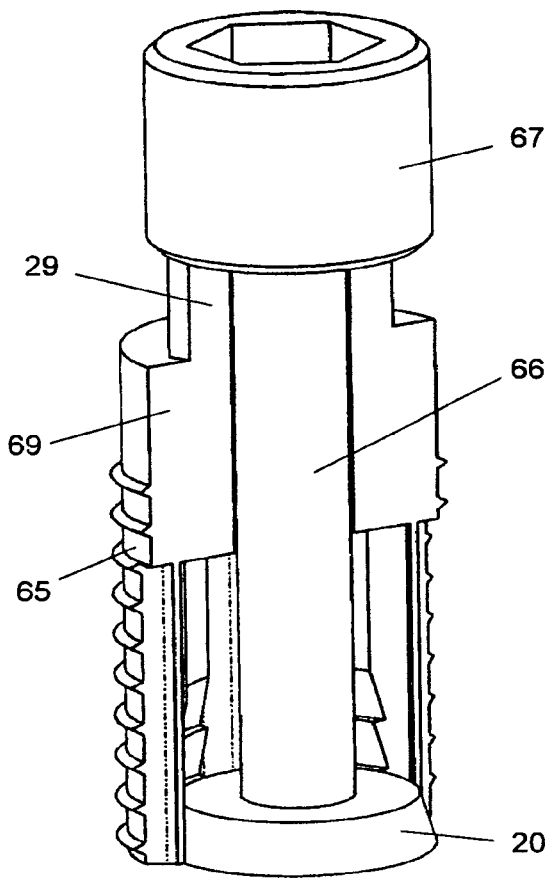
FIG. 12 is a perspective view of the dental implant of FIG. 8 with the outer body partially removed, showing a longitudinal displacing means.

In FIG. 12, screw 66 longitudinally extends from head 67 to expander 20, with which it may be threadably engaged, passing through head 29 and annular portion 69 of body 65. During rotation of head 67, e.g. with an Allen wrench, expander member 20 is longitudinally displaceable and body 65 is expandable. After expander 20 is immobilized, screw 65 may be removed therefrom and body 65 retains its expanded configuration.

Figure 13:
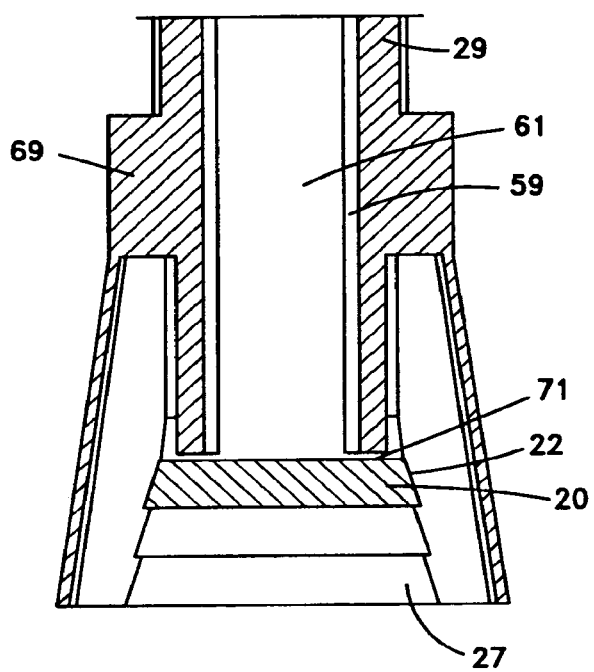
FIG. 13 is a longitudinal cross-sectional view of the implant of FIG. 1, illustrating the advantageously short longitudinal length of the implant.

Following removal of the screw from expander member 20, cavity 61 internal to annular portion 69 is accessible, as shown in FIG. 13. Internal threading 59, which encircles cavity 61 and longitudinally extends from head 29 to approximately the back of the most coronal step, e.g. with a gap of no more than 0.1 mm, is adapted for engagement with a prosthetic piece. It will therefore be appreciated that the body is of the smallest possible length, since expander 20 is not formed with external threading, and therefore the longitudinal dimension of the expander is equal to the longitudinal dimension of side 22 which contacts a step 27. In contrast, prior art expandable implants are normally formed with external threading for coupling with the inner surface of the outer body, extending from the coronal end 71 of the contact element of the expander which bears against the inner surface of deformable legs, and thereby increasing the length of the expander member and of the outer body.

The coefficient of friction between expander 20 and backs 27 is usually sufficiently high so as to provide a reactive force when screw 66 (FIG. 12) is rotated, in order to longitudinally displace the expander member. At times, however, due to the materials selected or due to the manufacturing tolerances, a sufficient rotational reactive force is not provided, and other means must be employed to prevent rotation of the expander member during longitudinal displacement.

Figure 14:
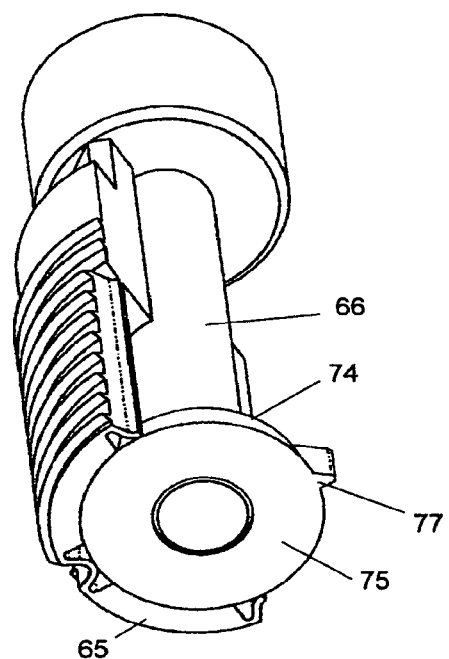
FIG. 14 is a perspective view of the implant of FIG. 8, showing means for restraining the rotation of an expander member.
Figure 15:
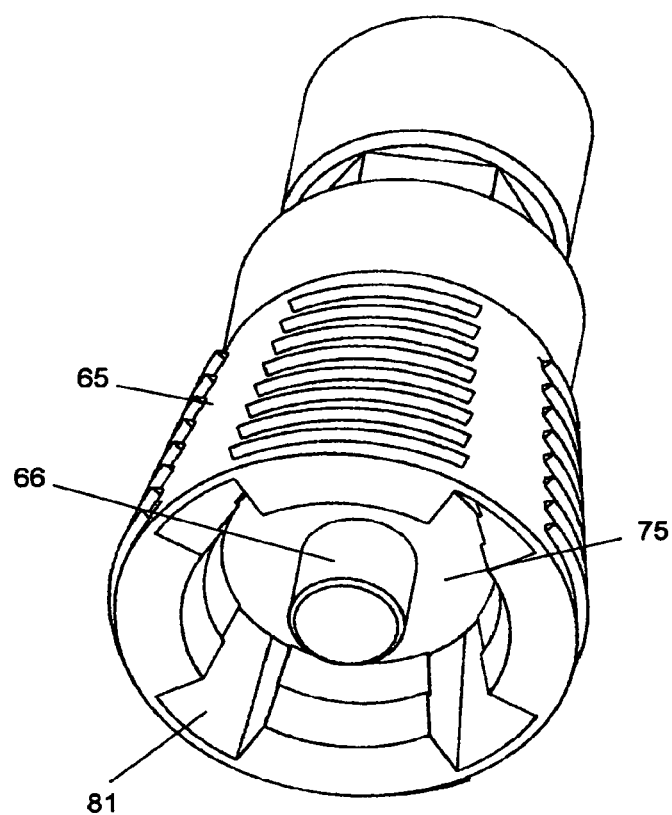
FIG. 15 is a perspective view of the implant of FIG. 8, showing means for restraining the rotation of an expander member.

FIGS. 14 and 15 illustrate an exemplary means of preventing rotation of the expander during longitudinal displacement. Side wall 74 of expander member 75 is formed with a plurality of substantially equally spaced pointed radial projections 77, as shown in FIG. 14, or circumferential projections, as shown in FIG. 15. Each projection is rotationally restrained by a similarly shaped groove, e.g. a circumferential groove 81 in FIG. 15, which is longitudinally formed in the inner surface of body 65. Upon rotation of screw 66, each projection is longitudinally displaced in a corresponding groove, while expander member 75 is prevented from being rotated.

The longitudinal displacing means may be a rod (not shown), or any other convenient arrangement, which couples with a suitable connecting device formed on the coronal end 71 (FIG. 13) of the expander device, as well known to those skilled in the art. The displacement means may be inserted within cavity 61. As the displacing means is coronally pulled, expander 20 is similarly coronally displaced and body 65 expands.

Figure 16:
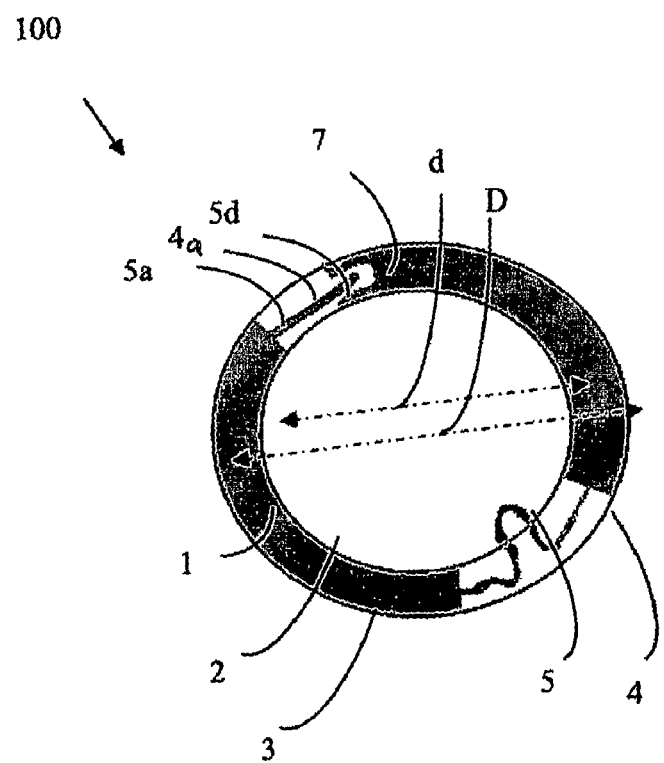
FIG. 16 is a lateral cross section of the implant's envelope in the apical area showing various possibilities of slit format; and, FIG. 17A is a longitudinal cross sections of the implant's envelope, containing integral step and the expander inside its barrel.

FIG. 16 illustrates a lateral cross section of the apical portion of the implant's envelope 1; envelope 1 has an inner diameter d and an outer diameter D. The wall of envelope 1 comprises slits 4 and lids 5 that are shown here in several possible formats; for example, lid 5 formed a continuous fold. Another possibility is represented in slit 4a wherein lid 5d is immobilized in one of its ends 5a, to the envelope's wall and at its other end moves freely in and out of a recess 7 formed in the opposite envelope's wall.

Figure 17A:
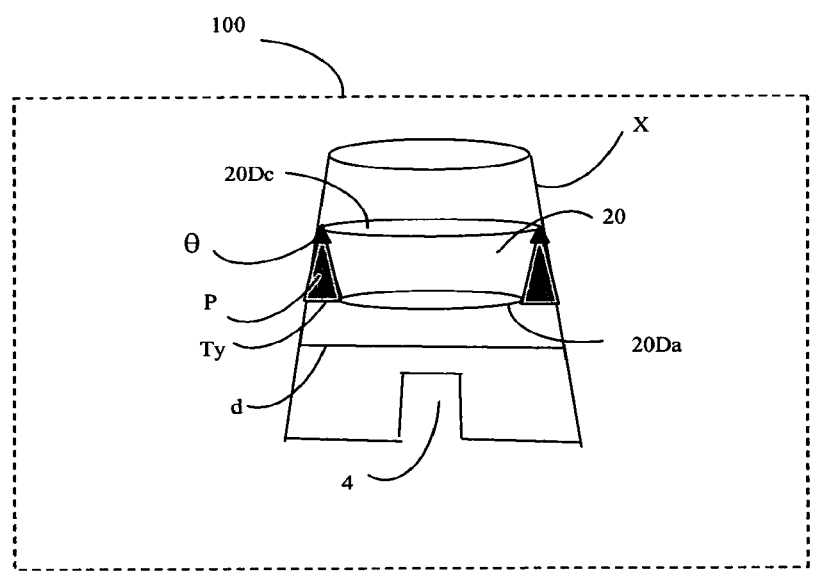
FIG. 17B is a longitudinal cross sections of the implant's envelope, containing integral step and the expander inside its barrel.
Figure 17B:
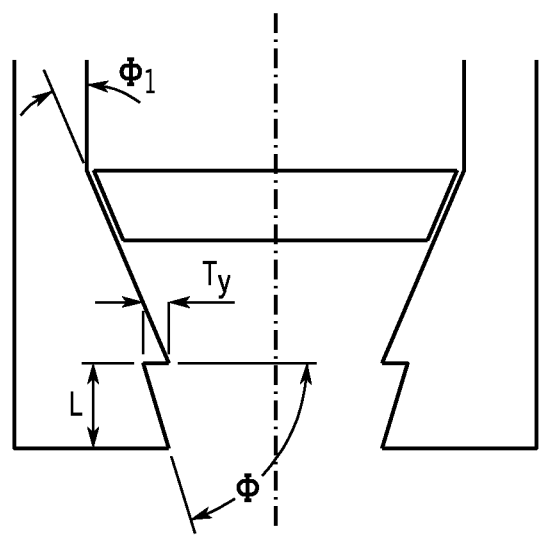

FIG. 17a illustrates a longitudinal cross section of the implant's envelope 1, containing integral step P and expander 20 inside its barrel. The envelope 1 comprises a slit 4, an apical inner diameter d, and a step P. The step P has a thickness of $T_P$, an angle θ, defining a slope of side L. Expander 20 is illustrated here as a conical shaped member with a coronal base $20D_C$ and an apical base $20D_A$. FIG. 17b illustrates a schematic presentation of the same, wherein angle θ1 is between about 3 to 60 degrees.

Figure 7:
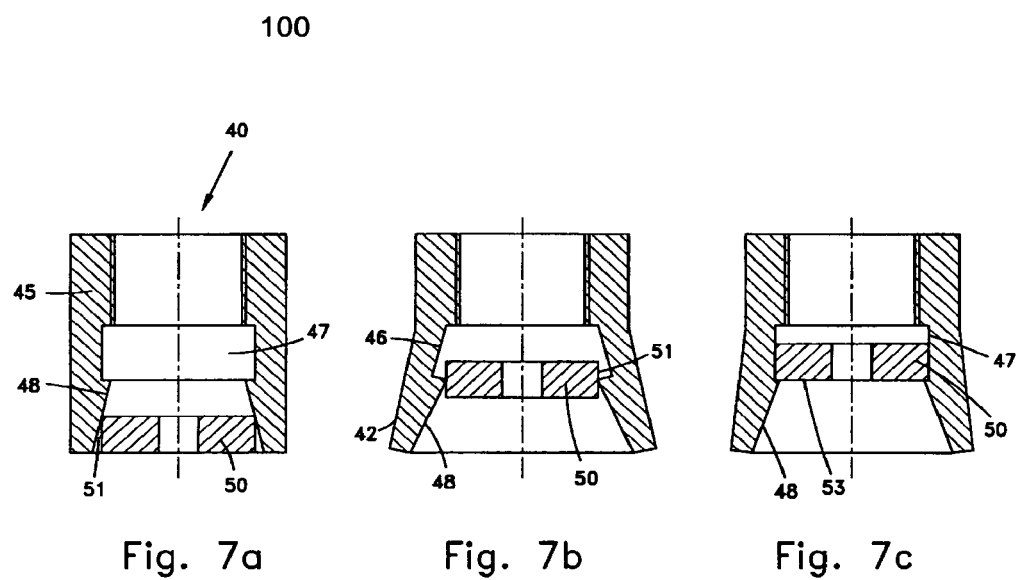
FIG. 7a is a longitudinal cross-sectional views of a dental implant, according to yet another embodiment of the invention, showing a first stage of longitudinal displacement of an expander member.
FIG. 7b is a longitudinal cross-sectional views of a dental implant, according to yet another embodiment of the invention, showing a second stage of longitudinal displacement of an expander member.
FIG. 7c is a longitudinal cross-sectional views of a dental implant, according to yet another embodiment of the invention, showing a third stage of longitudinal displacement of an expander member.
Figure 18:
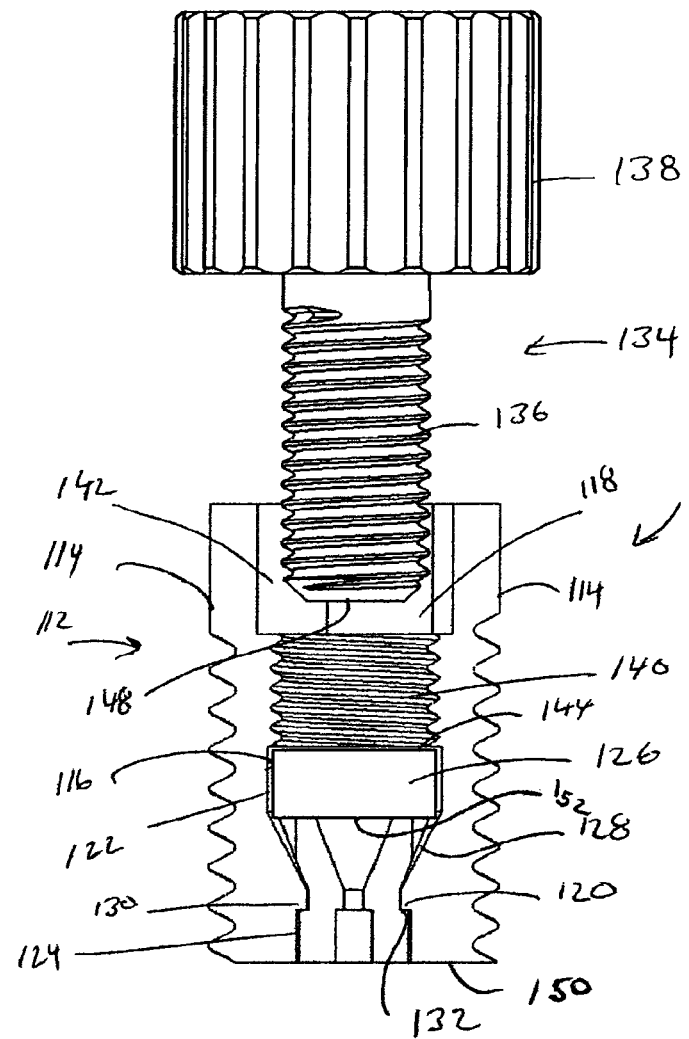
FIG. 18 is a cross sectional view of an insert.
Figure 19:
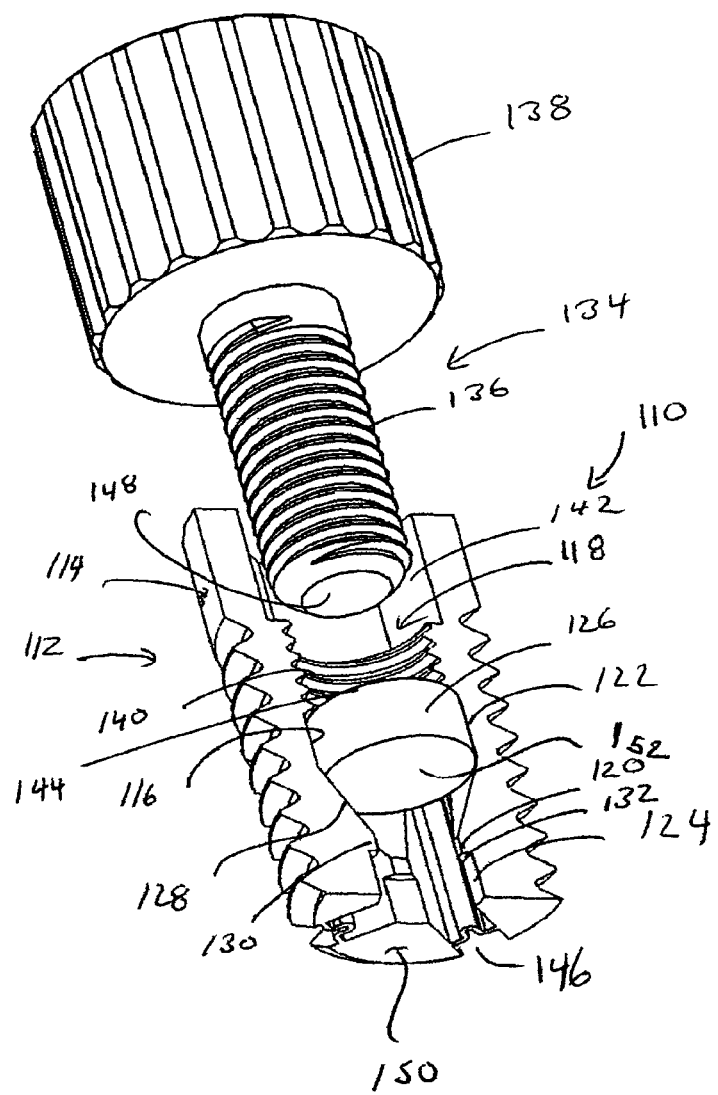
FIG. 19 is a perspective cross sectional view of the insert of FIG. 18.

FIGS. 18 and 19 illustrate a longitudinal cross section and perspective longitudinal cross-section of an implant 110. It is submitted that the implant illustrated in FIGS. 18 and 19 are fully supported by the description provided above. FIGS. 18 and 19 include unique reference numerals, however all of the features are disclosed in the Figs. and embodiments discussed above. Implant 110 includes a envelope 112 including an outer surface 114 and an inner surface 116 defining a barrel 118. At least one barrier 120 is located in barrel 118. The barrel includes two regions 122 and 124 located on opposite sides of barrier 120. An expander 126 is movable within the barrel 118 from the first region 122 toward the second region 124. An inwardly extending transition region 128 extends between the first region 122 and barrier 120. As expander 126 is moved from the first region 122 toward the second region 124 a portion of the envelope is forced radially outwardly allowing expander 126 to move from the first region 122 toward the second region 124. The insert is shown in its contracted configuration in FIGS. 18 and 19. The insert moves towards it expanded configuration as the expander is moved from the first region 122 toward the second region 124. The diameter of the first region 122 is greater than the diameter of the second region 124 when the insert is in the contracted position. Barrier 120 includes a step 130 having a ledge 132 extending away from the longitudinal axis of the insert. In one embodiment expander 126 has a frustoconical shape as described above with respect to the expander 20. However expander 126 may also have a cylindrical shape as illustrated in FIG. 7.

Expander 126 may be moved within barrel 118 by a longitudinal member 134 having a threaded portion 136 and a top portion 138. Longitudinal member 134 is threadably received in insert 110 via an internal threaded region 140. Internally threaded region 140 in one embodiment is located adjacent a coronal end 142 of insert 110. First region 122 may be threadless as is expander 126. In the contracted configuration an upper edge 144 located at the top of expander 126 is located adjacent threaded region 140. Longitudinal member 134 is threadably rotated within internal threaded region 140 until a bottom 148 longitudinal member 134 contacts the top of expander 126 and forces expander 126 toward the second region 124. A portion of envelope 112 radially expands outwardly as expander 126 moves toward barrier 120 allowing an upper edge 144 of expander 126 to pass barrier 120. Once expander 126 passes barrier 120, the radially expanding portion may move toward the longitudinal axis locking expander 126 within the second region 124. The movement of the radially expanding portion may result from the spring bias of the insert and/or external pressure exerted upon the insert by the bore wall of a patient. Ledge 132 prohibits expander 126 from moving from second region 124 toward first region 122. Longitudinal member 134 may then be removed independent of expander member 126 and insert 110 remains in an expanded configuration as shown in FIGS. 6c and 7c. A tooth prosthesis can then be threadably received within the internally threaded region 140 to secure the tooth prosthesis to the insert. In the expanded configuration the bottom 152 of expander 126 is adjacent the bottom 150 of insert 110. The location of bottom 152 proximate the bottom 150 of insert 110 provides a greater surface area for the insert in the bore of a patient. In one embodiment the length of the expander 126 as measured from the top to bottom of the insert is substantially the same as the length of second region 124.

Referring to FIGS. 6, 16, 18 and 19, top surface 144 of expander 126 faces the coronal portion 142 and bottom surface 152 faces the bottom of the envelope 150. The bottom surface 152 of expander 126 has a diameter that is less than or equal to the diameter of the bottom opening of the envelope when the expander is in second region 124. The envelope includes a first non-radially expandable portion and a second radially expandable portion extending therefrom. The bottom portion of the second radially expandable portion extends radially further than the top end of the second radially expandable portion in the expanded configuration. The folded 146 portion having a top portion proximate the top end of the second radially expandable portion and a bottom edge proximate the bottom portion of the second radially expandable portion. In one embodiment, the bottom surface of the expander is in the same plane as a bottom surface of the envelope when the expander is in the second region. In another embodiment, the bottom surface of the envelope does not extend over a bottom most surface of the expander when the expander is in the second region.

The radially expandable portion of insert 110 may include one or more expandable regions 146 formed arranged in a folded arrangement in the contracted configuration. The expandable regions extend by unfolding or becoming straighter as the insert is moved from a contracted configuration to an extended configuration. Expandable regions may also include a lid 5d extending in a slit 4 as discussed above.

The construction and arrangement of the elements of the insert as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited herein. For example, elements shown as integrally formed may be constructed of multiple parts or elements, the position of elements may be reversed or otherwise varied, and the nature or number of discrete elements or positions may be altered or varied. It should be noted that the elements and/or assemblies of the system may be constructed from any of a wide variety of materials that provide sufficient strength, durability, or biocompatibility. The various features described herein may be used alone or an any combination. For example, the use of a lid or thin walled region may used in a conventional prior art insert or may be used in conjunction with the barrier feature. Other substitutions, modifications, changes and omissions may be made in the design, operating conditions and arrangement of the preferred and other exemplary embodiments and medical procedures without departing from the scope of the present invention.

What is claimed is:

1. A dental implant system for placement within a jaw of a patient, the implant comprising;
    a dental implant having an envelope including an outer surface and an inner surface defining a barrel, the envelope having a coronal end and an opposing bottom end;
    the coronal end of the envelope including a female threaded portion;
    an expansion tool threadably received in the female threaded portion, the expansion tool having a proximal end and a distal end;
    at least one barrier located in the barrel at a predetermined location, the barrel having a first region on one side of the barrier and a second region on an opposing side of the barrier;
    an expander being positioned within the barrel;
    the distal end of the expansion tool contacting a first side of the expander and moving the expander from the first region to the second region;
    the expansion tool being removable from the female threaded region;
    a tooth prosthesis threadably secured to the female threaded region;
    the envelope including a radially expandable portion being radially expandable from a contracted configuration to an expanded configuration upon movement of the expander from each first region toward the corresponding second region, the radially expandable portion expanding a predetermined distance as the expander is moved from the first region to the second region.

2. The dental implant system of claim 1 wherein the at least one barrier is a step having a ledge portion extending away from a longitudinal axis of the barrel.

3. The dental implant system of claim 2, wherein the expander member is secured in a discrete predetermined location by the step located within the barrel, the step allowing the expander member to move only in a single direction.

4. The dental implant system of claim 3, wherein the at least one barrier is at least two steps.

5. The dental implant system of claim 4, wherein the expander member is adapted to be displaced along the longitudinal axis in a number of discrete locations equal to the number of steps.

6. The dental implant of system of claim 5, wherein each step is characterized by a side, depth, and angle defining a slope of the side.

7. A dental implant system for placement within a jaw of a patient, the implant comprising;
    a dental implant having an envelope including an outer surface and an inner surface defining a barrel, the envelope having a coronal end and an opposing bottom end;
    at least two barriers located in the barrel at predetermined locations, the barrel having a first region on one side of each barrier and a second region on an opposing side of each barrier;
    an expander member movable within the barrel predetermined distances along a longitudinal axis of the barrel from the first region to the second region of each barrier, each barrier prohibiting the expander member from moving from each respective second region to the first region;
    a tooth prosthesis secured to the coronal end;

the at least two barriers each including a step having a ledge portion extending away from a longitudinal axis of the barrel;

wherein the expander member is secured in a discrete predetermined location by the step located within the barrel, the step allowing the expander member to move only in a single direction;

wherein the expander member is adapted to be displaced along the longitudinal axis in a number of discrete locations equal to the number of steps;

each step is characterized by a side, depth, and angle defining a slope of the side;

wherein the envelope includes a radially expandable portion being radially expandable from a contracted configuration to an expanded configuration upon movement of the expander from each first region toward the corresponding second region, the radially expandable portion expanding a first distance as the expander is moved over the first step, the radially expandable portion expanding further as the expander is moved over the second step.

8. The dental implant system of claim 7, further including a longitudinal member being removably received through a coronal end of the envelope, the longitudinal member having sufficient length to operatively move the expander member from each first region to each second region.

9. The dental implant system of claim 8, wherein the envelope includes an internally threaded region proximate the coronal end of the envelope, the longitudinal member being threadably received in internally threaded region of the envelope, the longitudinal member being removable independent of the location of the expander member.

10. The dental implant system of claim 9, wherein the tooth prosthesis is threadably secured to the internally threaded portion upon removal of the longitudinal member.

11. The dental implant system of claim 10, wherein the expander is threadless and a barrel portion through which the expander member moves is threadless, the barrel moving non-rotationally from each first region to each second region.

12. The dental implant system of claim 11 wherein each first region is closer to the coronal region than each second region, the expander member moving downwardly along the longitudinal axis upon an application of force by the longitudinal member, the barrier prohibiting the expander member from moving from each second region toward each first region.

13. A dental implant system, comprising
a dental implant having an envelope including an outer surface and an inner surface defining a barrel, the envelope having a coronal end and an opposing bottom end the coronal end having a threaded region configured to receive a threaded portion of a tooth prosthesis;
a plurality of discrete barriers located in the barrel at predetermined locations, the barrel having a first region on one side of each of the barriers and a second region on an opposing side of each of the barriers;
an expander member movable within the barrel to a number of discrete positions proximate each barrier equal to the number of barriers;
the envelope including a radially expandable portion being radially expandable from a contracted configuration to a fixed number of discrete expanded configurations equal to the number of barriers upon movement of the expander from the first region toward the second region over each successive barrier, the radially expandable portion expanding a first distance as the expander is moved over the first barrier and a greater distance as the expander is moved over each additional barrier.

14. The dental implant system of claim 13 wherein the plurality of discrete barriers includes a step having a ledge portion extending away from a longitudinal axis of the barrel.

15. The dental implant of system of claim 14, wherein each step is characterized by a side, depth, and angle defining a slope of the side.

16. A method comprising;
drilling a bore within a jaw of a patient;
providing a dental implant having a coronal end and an elongated envelope having a barrel defining a longitudinal axis extending longitudinally therethrough, the envelope having a radially expandable portion having a predetermined number of barriers located therein the coronal end having a threaded region configured to receive a threaded portion of a tooth prosthesis;
placing the dental implant into the bore formed in a jaw of a patient;
moving an expander along the longitudinal axis across a first of the predetermined number of barriers forcing the radially expandable portion from a first contracted configuration to second predetermined expanded configuration, the expander being prohibited from moving back across the first barrier;
wherein if the predetermined number of barriers is great than 1, then repeating the step of moving the expander across the successive predetermined barriers, expanding the radially expandable portion further each time the extender is moved over each successive barrier until the radially expandable portion is at one of the desired predetermined expandable configurations.

17. The dental implant system of claim 16 wherein the at least one barrier is a step having a ledge portion extending away from a longitudinal axis of the barrel.

18. The dental implant of system of claim 17, wherein each step is characterized by a side, depth, and angle defining a slope of the side.

19. A method comprising:
drilling a bore within a jaw of a patient;
providing a dental implant including:
an envelope including an outer surface and an inner surface defining a barrel, the envelope having a coronal end and an opposing bottom end, the coronal end including a female threaded portion;
at least one barrier being positioned in the barrel at a predetermined location, the barrel having a first region on one side of the barrier and a second region on an opposing side of the barrier;
an expander being positioned within the barrel;
a radially expandable portion being radially expandable from a contracted configuration to an expanded configuration;
providing an expansion tool separate from the expander having a male threaded region and a distal end;
threading the expansion tool into the female threaded region, until the distal end of the expansion tool contacts the expander and the expander moves from the first region over the barrier toward the second region, expanding the radially expandable portion from the contracted configuration to the expanded configuration;
threadably removing the expansion tool from the female threaded region and the implant, the barrier prohibiting the expander member from moving from the second region toward the first region upon removal of the expansion tool from the implant; and
threading a tooth prosthesis to the female threaded region.

* * * * *